United States Patent [19]
Yano et al.

[11] Patent Number: 5,990,139
[45] Date of Patent: Nov. 23, 1999

[54] THIAZOLIDINEDIONE DERIVATIVES OR SALTS THEREOF AND PHARMACEUTICAL COMPOSITIONS CONTAINING THE SAME

[75] Inventors: Shingo Yano, Kawagoe; Kazuo Ogawa, Tokorozawa; Masakazu Fukushima, Hanno, all of Japan

[73] Assignee: Taiho Pharmaceutical Co., Ltd., Tokyo, Japan

[21] Appl. No.: 08/655,644

[22] Filed: May 30, 1996

[51] Int. Cl.⁶ .................... C07D 417/12; A61K 31/425
[52] U.S. Cl. .................... 514/369; 514/342; 546/280; 548/183
[58] Field of Search ............ 548/183; 546/280; 514/369, 342

[56] References Cited

FOREIGN PATENT DOCUMENTS

| | | |
|---|---|---|
| 645387A1 | 3/1995 | European Pat. Off. . |
| 07138258 | 5/1995 | Japan . |
| WO 9427995 | 12/1994 | WIPO . |

*Primary Examiner*—Robert Gerstl
*Attorney, Agent, or Firm*—Sughrue, Mion, Zinn, Macpeak & Seas, PLLC

[57] ABSTRACT

This invention relates to a thiazolidinedione derivative represented by the following formula (1):

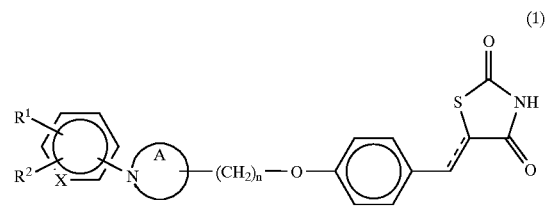

wherein $R^1$ and $R^2$ individually represent H, a halogen atom, or a halogen-substituted or -unsubstituted lower alkyl or alkoxy group, and $R^1$ and $R^2$ may be coupled together to form a ring of an alkylenedioxy chain, X represents a nitrogen atom or a CH group, A represents a substituted or unsubstituted imidazolidinone, pyrrolidinone, imidazole or pyrazole ring, or a salt thereof; and a pharmaceutical composition containing the thiazolidinedione derivative or a salt thereof. The above compound has excellent blood sugar-lowering action and blood lipid-lowering action and is useful as a therapeutic agent for diabetes.

8 Claims, No Drawings

THIAZOLIDINEDIONE DERIVATIVES OR SALTS THEREOF AND PHARMACEUTICAL COMPOSITIONS CONTAINING THE SAME

BACKGROUND OF THE INVENTION a) Field of the Invention

The present invention relates to novel thiazolidinedione derivatives and salts thereof. More specifically, this invention relates to thiazolidinedione derivatives or salts thereof which have excellent blood sugar-lowering activity and blood lipid-lowering activity, pharmaceutical compositions containing one or more of the compounds and methods for the treatment of diabetes.

b) Description of the Related Art

As synthetic hypoglycemic agents useful as therapeutic agents for diabetes, sulfonylurea preparations are widely used now. These sulfonylurea preparations, however, require very careful control during their use because they involve drawbacks such that they may cause critical and prolonged hypoglycemic symptoms or induce drug resistance.

There is accordingly the desire for development of a hypoglycemic agent serving as a substitute for such sulfonylurea preparations. Pharmaceuticals which can enhance the insulin sensitivity at peripheries and can show blood-sugar lowering action are increasingly attracting interests these days. However, these pharmaceuticals suffer from the disadvantage in that they produce undesirable side effects, and they do not posses sufficient blood sugar-lowering activity.

In addition, many cases of severe diabetics are accompanied by complications associated with hyperlipidemia. The development of a hypoglycemic agent which also displays blood-lipid lowering activity would be a useful pharmaceutical in the treatment of diabetes.

SUMMARY OF THE INVENTION

An object of the present invention is therefore to provide a novel compound which has excellent blood sugar-lowering activity and blood lipid-lowering activity, is capable of reducing undesirable side effects and is hence useful as a pharmaceutical agent for the therapy of diabetes.

With the foregoing circumstances in view, the present inventors have carried out an extensive investigation. As a result, it has been found that certain novel, specific thiazolidinedione derivatives and salts thereof have excellent blood sugar-lowering activity and blood lipid-lowering activity and are useful as pharmaceuticals, leading to the completion of the present invention.

The present invention therefore provides a thiazolidinedione derivative represented by the following formula (1):

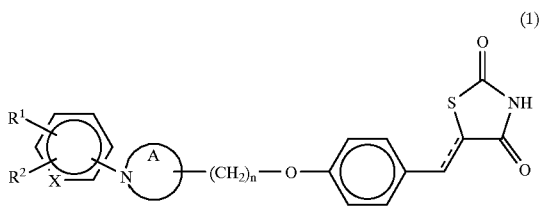

(1)

wherein $R^1$ and $R^2$ may be the same or different and individually represent a hydrogen atom, a halogen atom, a halogen-substituted or -unsubstituted lower alkyl group or a halogen-substituted or -unsubstituted lower alkoxyl group, and $R^1$ and $R^2$ may be coupled together to form a ring of an alkylenedioxy chain having 1 to 3 carbon atoms; X represents a nitrogen atom or a CH group; ... represents a single bond or a double bond; A represents a heterocycle selected from the following formula (a), (b), (c), (d), (e) or (f):

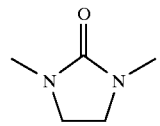

(a)

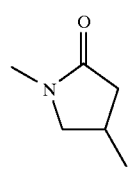

(b)

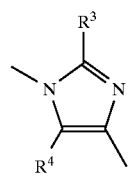

(c)

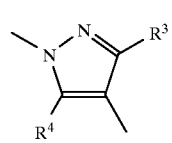

(d)

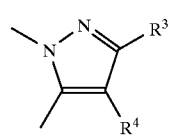

(e)

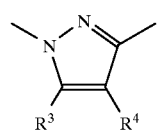

(f)

wherein $R^3$ and $R^4$ may be the same or different and individually represent a hydrogen atom or a lower alkyl group; and n stands for an integer of 1 to 4; or a salt thereof.

In addition, the present invention also provides a pharmaceutical composition which comprises an effective amount of the thiazolidinedione derivative or a salt thereof and a pharmacologically acceptable carrier.

The present invention also provides a pharmaceutical composition for the treatment of diabetes, which comprises an effective amount of the thiazolidinedione derivative or a salt thereof and a pharmacologically acceptable carrier.

Further, the present invention also provides a method of the treatment of diabetes, which comprises administering to a patient an effective amount of the thiazolidinedione derivative or a salt thereof.

Each thiazolidinedione derivative or a salt thereof according to the present invention has excellent blood-sugar lowering activity and blood-lipid lowering activity. It has good absorption into the body and has long-lasting drug efficacy. In addition, it has excellent excretion and low toxicity, so that it is useful as pharmaceuticals such as a diabetes treating agent, a hyperlipidemia treating agent, an arteriosclerosis preventive and treating agent, and an obesity preventive drug.

DETAILED DESCRIPTION OF THE INVENTION AND PREFERRED EMBODIMENTS

In the formula (1), examples of the halogen atoms represented by $R^1$ or $R^2$ include fluorine, chlorine, bromine and iodine atoms.

Examples of the lower alkyl groups represented by $R^1$, $R^2$, $R^3$ and $R^4$ include linear or branched $C_{1-6}$ alkyl groups such as methyl, ethyl, n-propyl, isopropyl, n-butyl, isobutyl, sec-butyl, tert-butyl, pentyl, hexyl and the like.

Illustrative examples of the halogen-substituted lower alkyl group include linear or branched $C_{1-6}$ alkyl groups containing 1–3 halogen atoms such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2-trichloroethyl, 3-fluoropropyl, 3,3,3-trichloropropyl, 4-chlorobutyl, 5-chloroheptyl, 6-chlorohexyl, 3-chloro-2-methylpropyl and the like.

Exemplary lower alkoxy groups include linear or branched $C_{1-6}$ alkoxy groups such as methoxy, ethoxy, n-propoxy, isopropoxy, n-butoxy, isobutoxy, sec-butoxy, tert-butoxy, n-pentyloxy, isopentyloxy, n-hexyloxy and the like.

Illustrative examples of the halogen-substituted lower alkoxy group include linear or branched $C_{1-6}$ alkoxy groups containing 1–3 halogen atoms such as chloromethoxy, bromomethoxy, iodomethoxy, fluoromethoxy, dichloromethoxy, dibromomethoxy, difluoromethoxy, trichloromethoxy, tribromomethoxy, trifluoromethoxy, 2-chloroethoxy, 2-bromoethoxy, 2-fluoroethoxy, 1,2-dichloroethoxy, 2,2-difluoroethoxy, 1-chloro-2-fluoroethoxy, 2,2,2-trifluoroethoxy, 2,2,2-trichloroethoxy, 3-fluoropropoxy, 3,3,3-trichloropropoxy, 4-chlorobutoxy, 5-chloropentyloxy, 6-chlorohexyloxy, 3-chloro-2-methylpropyloxy and the like.

Examples of the alkylenedioxy chain having 1 to 3 carbon atoms and formed of $R^1$ and $R^2$ coupled together include methylenedioxy, ethylenedioxy and propylenedioxy chains.

X represents a nitrogen atom (N) or CH. Of these, particularly preferred is the case that X is CH (namely, the ring is a benzene ring).

Of the heterocycles (a), (b), (c), (d), (e) and (f) represented by A, the heterocycles (a) and (d) are more preferred, with the heterocycle (d) being particularly preferred.

n denotes an integer of 1 to 4, more preferably 1 to 3, still more preferably 1 or 2, notably 1.

⋯ represents a single bond or a double bond. Of these, a single bond is more preferred.

More preferred specific examples of $R^1$ and $R^2$ include H, methyl, ethyl, trifluoromethyl, methoxy, trifluoromethoxy, Cl, F and methylenedioxy. More preferred specific examples of $R^3$ and $R^4$ include H and methyl.

Among the compounds represented by the formula (1), more preferred are those containing a heterocycle represented by the formula (a) or (d) as A, CH as X and a single bond as ⋯. Of these compounds, more preferred are those represented by formula (1) in which $R^1$ and $R^2$ are the same or different and individually represent a hydrogen atom or a halogen atom, A is a heterocycle represented by the formula (d), n stands for 1, X is CH and ⋯ is a single bond. Most preferred are those represented by formula (1) in which $R^1$ is a hydrogen atom, $R^2$ is a chlorine atom, A is a heterocycle represented by the formula (d) in which $R^3$ represents a hydrogen atom or a methyl group and $R^4$ represents a methyl group, n is 1, X is CH and ⋯ is a single bond.

Illustrative of the salt of the compound represented by the formula (1) according to the present invention are acid-addition salts and base salts which have been obtained by causing pharmacologically acceptable acids and basic compounds to act on the compound, respectively. Examples of the acid addition salts include salts of a compound of the formula (1), especially a compound containing a basic group such as an amino group or mono- or di-lower alkyl amino group with an acid such as an inorganic acid, e.g., hydrochloric acid, sulfuric acid, phosphoric acid or hydrobromic acid or an organic acid, e.g., oxalic acid, maleic acid, fumaric acid, malic acid, tartaric acid, citric acid, benzoic acid, acetic acid, p-toluenesulfonic acid or ethanesulfonic acid. Exemplary base salts include salts with an alkali metal or alkaline earth metal such as sodium, potassium, magnesium or calcium and organic salts with an amine such as ammonia, methylamine, dimethylamine, piperidine, cyclohexylamine or triethylamine.

The thiazolidinedione derivatives represented by the formula (1) have optical isomers. It is to be noted that these optical isomers are all embraced by the present invention. Further, the compounds of the present invention may exist in the form of hydrates or the like. These forms are also encompassed by the present invention.

The compound (1) of the present invention can be prepared, for instance, in accordance with the following Process A, using various compounds as raw materials:

Process A:

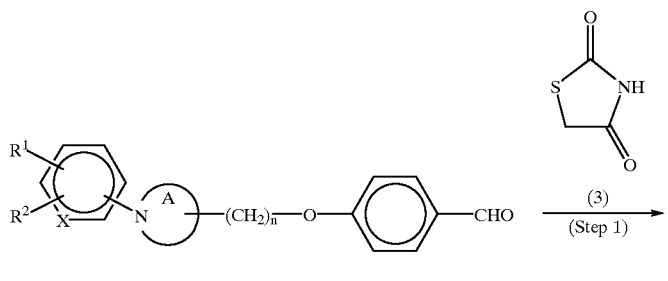

(2)

-continued

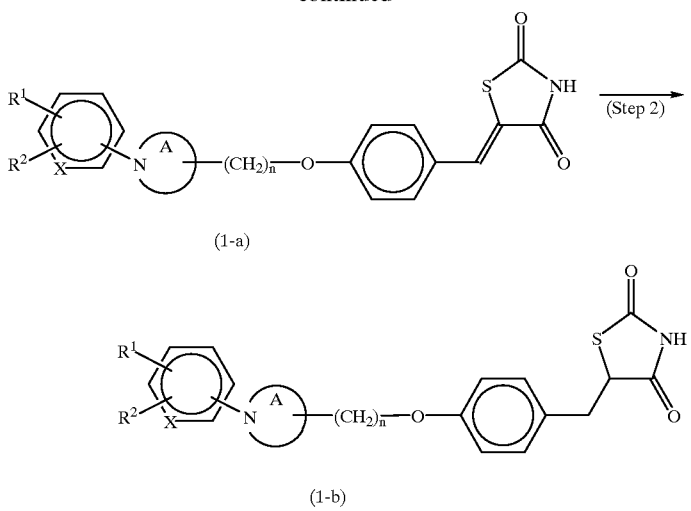

wherein $R^1$, $R^2$, X, A and n have the same meanings as defined above.

Namely, reaction of 2,4-thiazolidinedione (3) with a benzaldehyde derivative (2) in the presence of a basic compound provides a compound (1-a) according to the present invention. Further, its reduction provides a compound (1-b) according to the present invention.

Described in detail, the individual steps of Process A can be practiced as will be described below.

(Step 1)

The compound (1-a) according to the present invention can be prepared by reacting the compound represented by the formula (2) and 2,4-thiazolidinedione (3) in a suitable solvent in the presence of a basic compound.

No particular limitation is imposed on the solvent insofar as it takes no part in the reaction. Examples of the solvent include aromatic hydrocarbons such as benzene, toluene, xylene and the like; fatty acids such as formic acid, acetic acid, propionic acid and the like: ethers such as diethyl ether, tetrahydrofuran, dioxane, dimethoxyethane and the like; alcohols such as methanol, ethanol, propanol, 2-propanol, butanol and the like; aprotic polar solvents such as N,N-dimethylformamide, N,N-dimethylacetamide, acetonitrile, dimethyl sulfoxide, hexamethylphosphoric triamide and the like.

Illustrative basic compounds include organic basic compounds such as fatty acid alkali metal salts, e.g., sodium acetate and potassium acetate and tertiary amines, e.g., triethylamine and pyridine; and inorganic basic compounds such as alkali metal carbonates, e.g., sodium carbonate and potassium carbonate, alkali metal bicarbonates such as sodium bicarbonate and potassium bicarbonate, alkali metals, e.g., sodium and potassium, and alkali metal hydrides, e.g., sodium hydride. Upon reaction, the thiazolidinedione (3) may be used in an amount of 1 to 3 mole equivalents and the basic compound in an amount of 0.01 to 10 mole equivalents, preferably 0.05 to 3 mole equivalents, both per mole of the compound of the formula (2). The reaction temperature may range from 0° C. to the boiling point of the solvent or so, preferably from 60° C. to 140° C. The reaction time may range from 0.5 to 48 hours, preferably from 1 to 24 hours.

The compound (1-a) of the present invention available as described above has blood sugar-lowering activity by itself. However, this compound can be used as an intermediate after its isolation, or alternatively used without isolation to obtain the compound (1-b) of the present invention through the following step 2.

(Step 2)

The compound represented by the formula (1-b) can be prepared by catalytically reducing the compound represented by the formula (1-a) in the presence of a catalyst in an inert solvent.

No particular limitation is imposed on the solvent to be used here insofar as it takes no part in the reaction. For examples, ethyl acetate, methanol, tetrahydrofuran, 1,4-dioxane, N,N-dimethylformamide, acetic acid and the like can be used either singly or in combination. Usable examples of the catalyst include palladium carbon, platinum and the like. The hydrogen pressure may range from normal pressure to 500 atm, with a range of from normal pressure to 80 atm being particularly preferred. The reaction temperature may range from 0° C. to 100° C., especially from room temperature to 70° C. The reaction time may range from 0.5 to 48 hours, particularly from 2 to 24 hours.

The compound represented by the formula (2) can be prepared, for example, by the following Process B, Process C, Process D or Process E, using various materials as raw materials.

Process B:

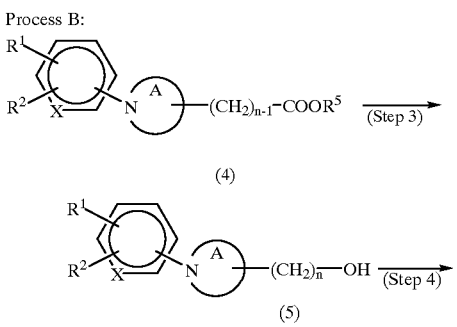

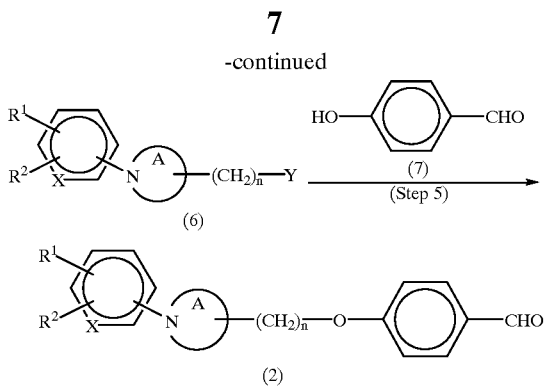

wherein $R^1$, $R^2$, A, X and n have the same meanings as defined above, $R^5$ represents a hydrogen atom or a lower alkyl group, and Y represents a halogen atom, a substituted or unsubstituted lower alkanesulfonyloxy group, or a substituted or unsubstituted lower arylsulfonyloxy group.

As examples of the lower alkyl group represented by $R^5$ and the halogen atom represented by Y in the compound represented by the formula (6), those exemplified above with respect to $R^1$ and $R^2$ can be mentioned. Illustrative of the substituted or unsubstituted lower alkanesulfonyloxy group are halogen-substituted or -unsubstituted $C_{1-6}$ alkanesulfonyloxy groups such as methanesulfonyloxy, ethanesulfonyloxy, propanesulfonyloxy, trifluoromethanesulfonyloxy groups and the like. On the other hand, illustrative of the substituted or unsubstituted lower arylsulfonyloxy group are arylsulfonyloxy groups which may be substituted by one or more $C_{1-6}$ alkyl atoms, halogen atoms or nitro groups, such as benzenesulfonyloxy, toluenesulfonyloxy, p-chlorobenzenesulfonyloxy, m-nitrobenzenesulfonyloxy groups and the like.

Described in detail, the individual steps of the above reaction scheme can be practiced as will be described below.
(Step 3)

The compound represented by the formula (5) can be prepared by reducing, in the presence of sodium boron hydride, lithium aluminum hydride or the like in an inert solvent, a known compound represented by the formula (4) and disclosed in a publication such as Japanese Patent Laid-Open (Kokai) No. 275666/1991, Journal of Heterocyclic Chemistry, 24, 1757–1763, 1987, Journal of Heterocyclic Chemistry, 24, 1669–1675, 1987, Synthesis, 753–755, 1986, Chemische Berichte, 116, 3039–3061, 1983, or Gazzetta Chimica Italiana, 70, 27–235, 1940 or a compound represented by the formula (4) and prepared by a conventionally-known process.

No particular limitation is imposed on the solvent insofar as it takes no part in the reaction. For example, ethers such as tetrahydrofuran, 1,4-dioxane, diethyl ether and the like and alcohols such as methanol, ethanol, propanol and the like can be used either singly or in combination. Regarding the proportions of the raw materials, sodium boron hydride, lithium aluminum hydride or the like may be used preferably in an amount of 0.5 to 10 mole equivalents per mole of the compound of the formula (4). The reaction temperature may range from 0° C. to 100° C., especially from 0° C. to 50° C. The reaction time may range from 0.1 to 24 hours, preferably from 0.5 to 6 hours.

The compound of the formula (5) available by the above reaction can be used in Step 4 with or without isolation.
(Step 4)

The compound represented by the formula (6) can be prepared by reacting the compound represented by the formula (5) with a halogenating agent, a halogen-substituted or -unsubstituted $C_{1-6}$ lower alkanesulfonyl chloride or a substituted or unsubstituted lower arylsulfonyl chloride in the presence or absence of an organic basic compound in an inert solvent.

This reaction is usually conducted in an appropriate solvent. No particular limitation is imposed on the solvent insofar as the solvent takes no part in the reaction. Examples of the solvent include aromatic hydrocarbons such as benzene, toluene, xylene and the like; tertiary amines such as triethylamine, pyridine and the like; ethers such as diethyl ether, tetrahydrofuran, 1,4-dioxane and the like; halogenated hydrocarbons such as dichloromethane, chloroform and the like; and aprotic polar solvents such as N,N-dimethylformamide, N,N-dimethylacetamide, acetonitrile, dimethyl sulfoxide and the like.

Examples of the organic basic compound include tertiary amines such as triethylamine, pyridine and the like. Illustrative of the halogenating agent include thionyl chloride, phosphorus oxychloride, phosphorus pentachloride, phosphorus tribromide and the like.

Examples of the halogen-substituted or -unsubstituted $C_{1-6}$ lower alkanesulfonyl chloride include methanesulfonyl chloride, ethanesulfonyl chloride, propanesulfonyl chloride, trifluoromethanesulfonyl chloride and the like. Examples of the substituted or unsubstituted lower arylsulfonyl chloride include benzenesulfonyl chloride, toluenesulfonyl chloride, p-chlorobenzenesulfonyl chloride, m-nitrobenzenesulfonyl chloride and the like.

Regarding the proportions of the raw materials, the organic basic compound may be used preferably in an amount of 1 to 3 mole equivalents per mole of the compound of the formula (5), and the halogenating agent, halogen-substituted or -unsubstituted $C_{1-6}$ lower alkanesulfonyl chloride or the substituted or unsubstituted lower arylsulfonyl chloride may be used preferably in an amount of 1 to 2 mole equivalents per mole of the compound of formula (5). The reaction temperature may range from 0° C. to the boiling point of the solvent or so, especially from 0° C. to 100° C. The reaction time may range from 0.1 to 24 hours, especially from 0.5 to 3 hours.

The compound of the formula (6) available by the above reaction can be used in Step 5 with or without isolation.
(Step 5)

The compound represented by the formula (2) can be prepared by reacting benzaldehyde (7) with the compound represented by the formula (6) in a suitable solvent in the presence of a basic compound.

No particular limitation is imposed on the solvent insofar as the solvent takes no part in the reaction. Examples of the solvent include ethers such as diethyl ether, tetrahydrofuran, 1,4-dioxane and the like; halogenated hydrocarbons such as dichloromethane, chloroform and the like; amines such as pyridine, piperidine, triethylamine and the like; alkyl ketones such as acetone, methyl ethyl ketone, methyl isobutyl ketone and the like; alcohols such as methanol, ethanol, propanol and the like; and aprotic polar solvents such as N,N-dimethylformamide, N,N-dimethylacetamide, acetonitrile, dimethyl sulfoxide, hexamethylphosphoric triamide and the like.

Examples of the basic compound include organic basic compounds such as tertiary amines, e.g., triethylamine, pyridine and the like; and inorganic basic compounds such as alkali metal carbonates, e.g., sodium carbonate, potassium carbonate and the like, alkali metal bicarbonates, e.g., sodium bicarbonate, potassium bicarbonate and the like; alkali metal hydroxides, e.g., sodium hydroxide, potassium hydroxide and the like; alkali metals, e.g., sodium, potassium and the like; and alkali metal hydrides, e.g., sodium hydride and the like. No solvent may be needed when an organic basic compound is employed.

Regarding the proportions of the raw materials, benzaldehyde (7) may be used in an amount of 1 to 2 mole equivalents and the basic compound in an amount of 1 to 5 mole equivalents, preferably 1–2 mole equivalents, both per mole of the compound of the formula (6). The reaction temperature may range from 0° C. to the boiling point of the solvent or so, preferably from 0° C. to 80° C. The reaction time may range preferably from 0.5 to 48 hours, especially from 1 to 24 hours.

The compound of the formula (2) available by the above reaction can be used in Step 1 with or without isolation.

Process C:

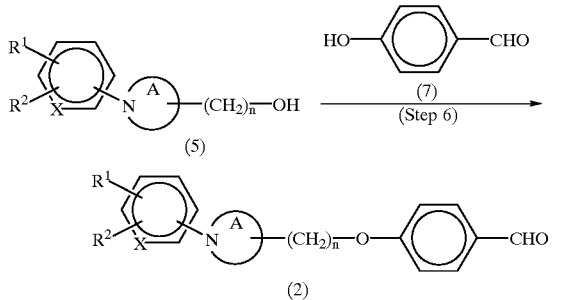

wherein $R^1$, $R^2$, A, X and n have the same meanings as defined above.

Described in detail, the individual steps of the above reaction scheme can be practiced as will be described below.

(Step 6)

The compound represented by the formula (2) can be prepared by reacting the compound represented by the formula (5) and benzaldehyde (7) in a suitable solvent in the presence of triphenylphosphine or diethyl azodicarboxylate.

No particular limitation is imposed on the solvent insofar as the solvent takes no part in the reaction. Examples of the solvent include ethers such as diethyl ether, tetrahydrofuran, 1,4-dioxane and the like; halogenated hydrocarbons such as dichloromethane, chloroform and the like; alkylketones such as acetone, methyl ethyl ketone, methyl isobutyl ketone and the like; and aprotic polar solvents such as N,N-dimethylformamide, N,N-dimethylacetamide, acetonitrile, dimethyl sulfoxide, hexamethylphosphoric triamide and the like.

Regarding the proportions of the raw materials, benzaldehyde (7) may be used in an amount of 1 to 2 mole equivalents and triphenylphosphine and diethylazodicarboxylate, each, in an amount of 1 to 5 mole equivalents, preferably 1–2 mole equivalents, all per mole of the compound of the formula (5). The reaction temperature may range from 0° C. to the boiling point of the solvent or so, preferably from 0° C. to 80° C. The reaction time may range from 0.25 to 48 hours, preferably from 0.5 to 8 hours.

The compound of the formula (2) available by the above reaction can be used in Step 1 with or without isolation.

Process D:

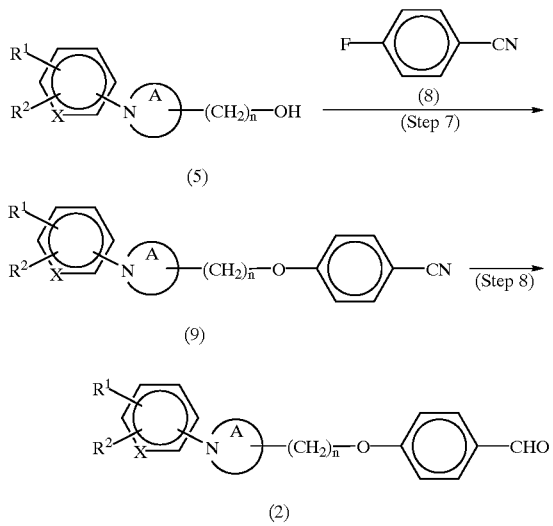

wherein $R^1$, $R^2$, X, A and n have the same meanings as defined above.

More specifically, the individual steps of the above reaction scheme can be practiced as will be described below.

(Step 7)

The compound represented by the formula (9) can be prepared by reacting p-fluorobenzonitrile (8) and the compound represented by the formula (5) in a suitable solvent in the presence of a basic compound.

No particular limitation is imposed on the solvent insofar as the solvent takes no part in the reaction. Examples of the solvent include ethers such as diethyl ether, tetrahydrofuran, 1,4-dioxane and the like; halogenated hydrocarbons such as dichloromethane, chloroform and the like; amines such as pyridine, piperidine, triethylamine and the like; alkylketones such as acetone, methyl ethyl ketone, methyl isobutyl ketone and the like; alcohols such as methanol, ethanol, propanol and the like; and aprotic polar solvents such as N,N-dimethylformamide, N,N-dimethylacetamide, acetonitrile, dimethyl sulfoxide, hexamethylphosphoric triamide and the like.

Examples of the basic compound include organic basic compounds such as tertiary amines, e.g., triethylamine, pyridine and the like; and inorganic basic compounds such as alkali metal carbonates, e.g., sodium carbonate, potassium carbonate and the like, alkali metal bicarbonates, e.g., sodium bicarbonate, potassium bicarbonate and the like; alkali metal hydroxides, e.g., sodium hydroxide, potassium hydroxide and the like; alkali metals, e.g., sodium, potassium and the like; and alkali metal hydrides, e.g., sodium hydride and the like. No solvent may be needed when an organic basic compound is employed. Regarding the proportions of the raw materials, p-fluorobenzonitrile (8) may be used in an amount of 1 to 2 mole equivalents and the basic compound in an amount of 1 to 5 mole equivalents, preferably 1 to 2 mole equivalents, both per mole of the compound of the formula (5). The reaction temperature may range from 0° C. to the boiling point of the solvent or so, especially from 0° C. to 80° C. The reaction time may range from 0.5 to 48 hours, notably from 1 to 8 hours.

The compound of the formula (9) available by the above reaction can be used in Step 8 with or without isolation.

(Step 8)

The compound represented by the formula (2) can be obtained by causing Raney nickel to act on the compound represented by the formula (9) in a suitable inert solvent.

No particular limitation is imposed on the solvent insofar as it takes no part in the reaction. Examples of the solvent include formic acid, acetic acid, water and mixed solvents of these organic solvents with water.

Regarding the proportions of the raw materials, Raney nickel may be used in an amount of 0.5 to 10 grams, preferably 1 to 3 grams per gram of the compound of the formula (9). The reaction temperature may range from 0° C. to the boiling point of the solvent or so, preferably from 50° C. to 100° C. The reaction time may range from 0.5 to 12 hours, especially from 1 to 6 hours.

The compound of the formula (2) available by the above reaction can be used in Step 1 with or without isolation.

Process E:

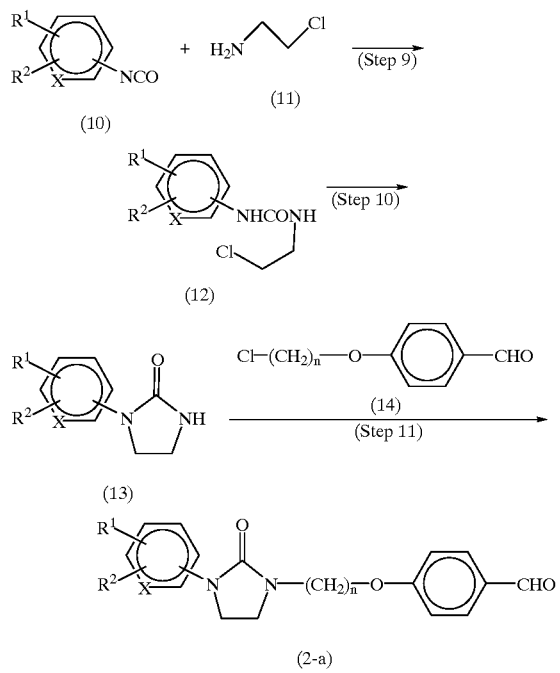

wherein $R^1$, $R^2$, X, A and n have the same meanings as defined above.

Described in detail, the individual steps of the above reaction scheme can be practiced as will be described below.

(Step 9)

The compound represented by the formula (12) can be obtained by reacting the compound represented by the formula (10) with the known compound represented by the formula (11).

This reaction is usually conducted in an appropriate solvent. No particular limitation is imposed on the solvent insofar as the solvent takes no part in the reaction. Examples of the solvent include aromatic hydrocarbons such as benzene, toluene, xylene and the like; ethers such as diethyl ether, tetrahydrofuran, 1,4-dioxane and the like; halogenated hydrocarbons such as dichloromethane, chloroform and the like; alkyl ketones such as acetone, methyl ethyl ketone, methyl isobutyl ketone and the like; and aprotic polar solvents such as N,N-dimethylformamide, N,N-dimethylacetamide, acetonitrile, dimethyl sulfoxide and the like.

Regarding the proportions of the raw materials, the compound of the formula (11) may be used preferably in an amount of 1 to 3 mole equivalents per mole of the compound of the formula (10). The reaction temperature may range from 0° C. to the boiling point of the solvent or so, preferably from 10° C. to 50° C. The reaction time may range preferably from 0.1 to 6 hours, especially from 0.5 to 2 hours.

The compound of the formula (12) available by the above reaction can be used in Step 10 with or without isolation.

(Step 10)

The compound represented by the formula (13) can be obtained by reacting the compound represented by the formula (12) with a basic compound in a suitable solvent.

No particular limitation is imposed on the solvent insofar as it takes no part in the reaction. Examples of the solvent include aromatic hydrocarbons such as benzene, toluene, xylene and the like; ethers such as diethyl ether, tetrahydrofuran, 1,4-dioxane and the like; halogenated hydrocarbons such as dichloromethane, chloroform and the like; alkylketones such as acetone, methyl ethyl ketone, methyl isobutyl ketone and the like; aprotic polar solvents such as N,N-dimethylformamide, N,N-dimethylacetamide, acetonitrile, dimethyl sulfoxide and the like. Examples of the basic compound include organic basic compounds such as tertiary amines, e.g., triethylamine, pyridine and the like; and inorganic basic compounds such as alkali metal carbonates, e.g., sodium carbonate, potassium carbonate and the like, alkali metal bicarbonates, e.g., sodium bicarbonate, potassium bicarbonate and the like; alkali metal hydroxides, e.g., sodium hydroxide, potassium hydroxide and the like; alkali metals, e.g., sodium, potassium and the like; and alkali metal hydrides, e.g., sodium hydride and the like.

Regarding the proportions of the raw materials, the basic compound may be used in an amount of 1 to 10 mole equivalents, more preferably 1 to 3 mole equivalents per mole of the compound of the formula (12). The reaction temperature may range preferably from 0° C. to the boiling point of the solvent or so, especially from 0° C. to 80° C. The reaction time may range preferably from 0.5 to 48 hours, especially from 1 to 24 hours.

The compound of the formula (13) available by the above reaction can be used in Step 11 with or without isolation.

(Step 11)

The compound represented by the formula (2-a) can be obtained by reacting the compound represented by the formula (13) and the compound represented by the formula (14) in a suitable solvent in the presence of a basic compound.

No particular limitation is imposed on the solvent insofar as it takes no part in the reaction. Examples of the solvent include aromatic hydrocarbons such as benzene, toluene, xylene and the like; ethers such as diethyl ether, tetrahydrofuran, 1,4-dioxane and the like; halogenated hydrocarbons such as dichloromethane, chloroform and the like; alkylketones such as acetone, methyl ethyl ketone, methyl isobutyl ketone and the like; and aprotic polar solvents such as N,N-dimethylformamide, N,N-dimethylacetamide, acetonitrile, dimethyl sulfoxide and the like. Examples of the basic compound include organic basic compounds such as tertiary amines, e.g., triethylamine, pyridine and the like; and inorganic basic compounds such as alkali metal carbonates, e.g., sodium carbonate, potassium carbonate and the like, alkali metal bicarbonates, e.g., sodium bicarbonate, potassium bicarbonate and the like; alkali metal hydroxides, e.g., sodium hydroxide, potassium hydroxide and the like; alkali metals, e.g., sodium, potassium and the like; and alkali metal hydrides, e.g., sodium hydride and the like.

Regarding the proportions of the raw materials, the compound of the formula (14) may be used preferably in an amount of 1 to 2 mole equivalents and the basic compound in an amount of 1 to 5 mole equivalents, more preferably 1 to 2 mole equivalents, both, per mole of the compound of the formula (13). The reaction temperature may range preferably from 0° C. to the boiling point of the solvent or so, especially from 0° C. to 50° C. The reaction time may range preferably from 0.5 to 48 hours, especially from 1 to 24 hours.

The compound of the formula (2-a) available by the above reaction can be used in Step 1 with or without isolation.

Further, the compound represented by the formula (5-a) as a preparation intermediate can be obtained by Process F which will be described below.

Process F:

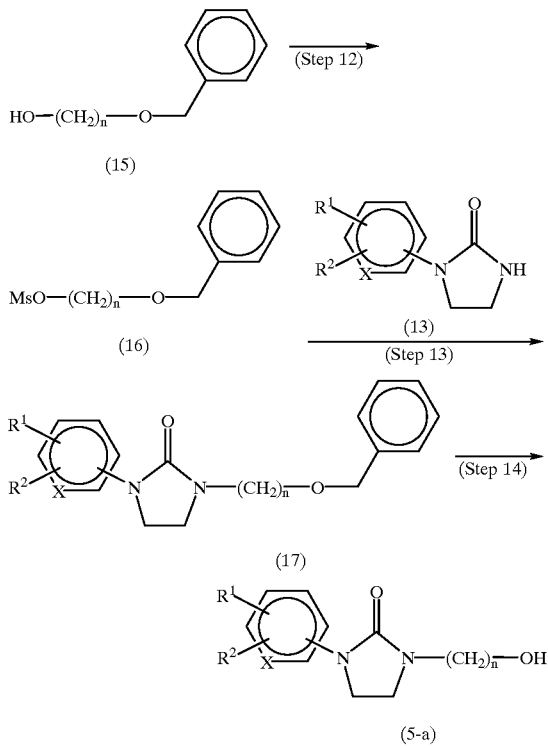

wherein $R^1$, $R^2$, X and n have the same meanings as defined above.

Described in more detail, the individual steps of the above reaction scheme can be practiced as will be described below.

(Step 12)

The compound represented by the formula (16) can be obtained by reacting the known compound represented by the formula (15) with methanesulfonyl chloride and a basic compound in a suitable solvent.

No particular limitation is imposed on the solvent insofar as it takes no part in the reaction. Examples of the solvent include aromatic hydrocarbons such as benzene, toluene, xylene and the like; ethers such as diethyl ether, tetrahydrofuran, 1,4-dioxane and the like; halogenated hydrocarbons such as dichloromethane, chloroform and the like; alkylketones such as acetone, methyl ethyl ketone, methyl isobutyl ketone and the like; and aprotic polar solvents such as N,N-dimethylformamide, N,N-dimethylacetamide, acetonitrile, dimethyl sulfoxide and the like. Examples of the basic compound include organic basic compounds such as tertiary amines, e.g., triethylamine, pyridine and the like.

Regarding the proportions of the raw materials, the basic compound may be used in an amount of 1 to 10 mole equivalents, more preferably 1 to 3 mole equivalents per mole of the compound of the formula (15). The reaction temperature may range preferably from 0° C. to the boiling point of the solvent or so, especially from 0° C. to 80° C. The reaction time may range preferably from 0.1 to 24 hours, especially from 0.5 to 6 hours.

The compound of the formula (16) available by the above reaction can be used in Step 13 with or without isolation.

(Step 13)

The compound represented by the formula (17) can be obtained by reacting the compound represented by the formula (16) with the compound represented by the formula (13) in a suitable solvent in the presence of a basic compound.

No particular limitation is imposed on the solvent insofar as it takes no part in the reaction. Examples of the solvent include ethers such as diethyl ether, tetrahydrofuran, 1,4-dioxane and the like; halogenated hydrocarbons such as dichloromethane, chloroform and the like; amines such as pyridine, piperidine, triethylamine and the like; alkylketones such as acetone, methyl ethyl ketone, methyl isobutyl ketone and the like; and aprotic polar solvents such as N,N-dimethylformamide, N,N-dimethylacetamide, acetonitrile, dimethyl sulfoxide, hexamethylphosphoric triamide and the like.

Examples of the basic compound include organic basic compounds such as tertiary amines, e.g., triethylamine, pyridine and the like; and inorganic basic compounds such as alkali metal carbonates, e.g., sodium carbonate, potassium carbonate and the like, alkali metal bicarbonates, e.g., sodium bicarbonate, potassium bicarbonate and the like; alkali metal hydroxides, e.g., sodium hydroxide, potassium hydroxide and the like; alkali metals, e.g., sodium, potassium and the like; and alkali metal hydrides, e.g., sodium hydride and the like. No solvent may be needed when an organic basic compound is employed.

Regarding the proportions of the raw materials, the compound of the formula (13) may be used in an amount of 1 to 1.5 mole equivalents and the basic compound in an amount of 1 to 5 mole equivalents, more preferably 1 to 2 mole equivalents, both, per mole of the compound of the formula (16). The reaction temperature may range preferably from 0° C. to the boiling point of the solvent or so, especially from 0° C. to 80° C. The reaction time may range preferably from 0.5 to 48 hours, especially from 1 to 24 hours.

The compound of the formula (17) available by the above reaction can be used in Step 14 with or without isolation.

(Step 14)

The compounds represented by the formula (5-a) can be prepared by subjecting the compound represented by the formula (17) to catalytic reduction in an inert solvent in the presence of a catalyst.

No particular limitation is imposed on the solvent insofar as it takes no part in the reaction. Illustrative solvents include ethyl acetate, methanol, tetrahydrofuran, 1,4-dioxane, N,N-dimethylformamide and acetic acid. They can be used either singly or in combination. Examples of the catalyst include palladium carbon and platinum. The hydrogen pressure may range from normal pressure to 500 atm., preferably from normal pressure to 80 atm. The reaction temperature may range preferably from 0° C. to 100° C., especially from room temperature to 70° C. The reaction time may range preferably from 0.5 to 48 hours, notably from 2 to 24 hours.

The compound of the formula (5-a) available by the above reaction can be used in Step 4, Step 6 or Step 7 with or without isolation.

The compound (1) of this invention obtained by Process A can be isolated by an ordinary separation method, for example, column chromatography, recrystallization or vacuum distillation.

The compound (1) of the present invention obtained as described above has excellent blood sugar-lowering action and blood lipid-lowering action and also has good absorption into the body and long-lasting drug efficacy. Moreover, it has excellent excretion and low toxicity, so that it is useful as pharmaceuticals for the treatment of diabetes and hyperlipidemia, for the prevention and treatment of arteriosclerosis, and for the purpose of anti-obesity.

Using appropriate pharmacologically acceptable carriers, the pharmaceutical composition according to the present invention can be formulated into various dosage forms by usual methods. Carries that are widely employed in ordinary pharmaceuticals include, for example, excipients, binders, disintegrators, lubricants, coloring matters, taste corrigents, smell corrigents, surfactants, etc.

No particular limitation is imposed on the dosable unit form upon using the pharmaceutical composition according to the present invention as a therapeutic agent for mammals including human. A desired dosable unit form can be chosen according to the object of treatment. Specific examples include non-parenteral preparations such as injections, suppositories, external preparations (ointments, plasters and the like) and aerosols; and oral preparations such as tablets, coated tablets, powders, granules, capsules, solutions, pills, suspensions and emulsions.

The above-described various compositions can be produced by methods known per se in the present field of art. Upon formulation into oral solid preparations, usable examples of carriers include excipients such as lactose, sucrose, sodium chloride, glucose, urea, starch, calcium carbonate, kaolin, crystalline cellulose, silicic acid, methyl cellulose, glycerin, sodium alginate, gum arabic and the like; binders such as simple syrup, glucose solution, starch solution, gelatin solution, polyvinyl alcohol, polyvinyl ether, polyvinyl pyrrolidone, carboxymethyl cellulose, shellac, methyl cellulose, ethyl cellulose, hydroxypropyl cellulose, water, ethanol, potassium phosphate and the like; disintegrators such as dried starch, sodium alginate, powdered agar, powdered laminarin, sodium bicarbonate, calcium carbonate, polyoxyethylene sorbitan fatty acid esters, sodium lauryl sulfate, stearic acid monoglyceride, starch, lactose and the like; disintegration suppressors such as sucrose, stearic acid, cacao butter, hydrogenated oils and the like; absor-befacients such as quaternary ammonium salts, sodium lauryl sulfate and the like; humectants such as glycerin, starch and the like; adsorbents such as starch, lactose, kaolin, bentonite, colloidal silicic acid and the like; and lubricants such as purified talc, stearate salts, powdered boric acid and polyethylene glycol. Further, tablets may be formed into those applied with conventional coatings as needed, for example, sugar-coated tablets, gelatin-coated tablets, enteric-coated tablets, film-coated tablets, double-layer tablets and multi-layer tablets.

Examples of carriers usable upon formulation into the form of pills include excipients such as glucose, lactose, starch, cacao butter, hydrogenated vegetable oils, kaolin, talc and the like; binders such as powdered gum arabic, powdered tragacanth, gelatin, ethanol and the like; and disintegrators such as laminarin, agar and the like.

Capsules can be formulated by mixing the compound of the present invention with one or more of the above-exemplified various carriers and then filling the resultant mixture in hard gelatin capsules, soft capsules or the like. As a carrier upon formulation into the form of suppositories, it is possible to use, for example, polyethylene glycol, cacao butter, lanolin, a higher alcohol, an ester of a higher alcohol, gelatin, semisynthetic glyceride, "Witepsol" (trade mark; product of Dynamit Nobel Corp.) and the like by adding an appropriate absorption promoter thereto.

Usable examples of carriers upon formulation into the form of injections include diluents such as water, ethyl alcohol, Macrogol, propylene glycol, ethoxylated isostearyl alcohol, polyoxylated isostearyl alcohol, polyoxyethylene sorbitan fatty acid esters and the like; pH regulators or buffers such as sodium citrate, sodium acetate, sodium phosphate and the like; and stabilizers such as sodium pyrosulfite, ethylenediamine tetraacetate, thioglycolic acid, thiolactic acid and the like. In this case, such pharmaceutical preparations may contain sodium chloride, glucose or glycerin in an amount sufficient to prepare isotonic solutions. Further, conventional solubilizing aids, soothing agents, local anesthetics and the like may also be added. By adding these carriers, subcutaneous, intramuscular and intravenous injections can be produced in a manner known per se in the art.

Liquid preparations can be water-base or oil-base suspensions, solutions, syrups or elixirs. Using ordinary carriers, they can be formulated in a manner known per se in the art.

Upon formulation into the form of an ointment, for example, a paste, cream or gel, a base, a stabilizer, a moisturizing agent, an antiseptic and the like are proportioned as needed and are mixed and formulated into the dosable form by conventional methods. Usable examples of the base include white petrolatum, paraffin, glycerin, cellulose derivatives, polyethylene glycol, silicone, bentonite and the like. Illustrative usable examples of the antiseptic include methyl paraoxybenzoate, ethyl paraoxybenzoate, propyl paraoxybenzoate and the like.

For the formulation of a plaster, it is only necessary to coat a conventional backing material with the above-described ointment, cream, gel or paste. Suitable examples of the backing material include woven fabrics or nonwoven fabrics of cotton, rayon or chemical fibers, and films or foamed sheets of soft PVC, polyethylene or polyurethane.

The amount of the invention compound to be incorporated in each of the above-described compositions varies depending on the preparation form, the administration route, dosage regimen and the like, cannot be determined in any wholesale manner, and can be chosen from a wide range as desired. In general, however, it is desired to incorporate the inventive compound in an amount of about 1 to 70 wt. %.

No particular limitation is imposed on the administration method for the above composition. An administration method such as enteral administration, oral administration, rectal administration, intraoral administration or percutaneous administration is determined as desired depending on the form of the preparation, the age, sex and other conditions of the patient, the severity of a symptom of the patient, and the like. For example, oral administration may be used for tablets, pills, solutions, suspensions, emulsions, granules and capsules, whereas rectal administration may be relied upon for suppositories. In the case of injections, they can be intravenously administered either alone or as mixtures with an ordinary fluid replacement such as glucose or an amino acid or, if necessary, can be administered by themselves intra-arterially, intramuscularly, intracutaneously, subcutaneously or intraperitoneally. Ointments are coated onto skin or intraoral mucosa.

The dose of the active ingredient in the composition according to the present invention is suitably chosen depending on the administration method, the age and sex of the patient, the severity of the disease, the kind of the invention compound so administered, and other conditions. As a standard, it may generally be preferred to choose a dose of about 0.1 to 5,000 mg/kg/day, preferably about 1 to 1,000 mg/kg/day. These compositions according to the present invention can each be administered once a day or in about 2 to 4 portions in a day.

EXAMPLES

The present invention will hereinafter be described more specifically by Referential Examples and Examples. It is, however, to be borne in mind that the present invention is by no means limited to or by them.

Referential Example 1

Synthesis of 1-(4-ethylphenyl)-2-imidazolidinone (Compound No. 1)

To a solution of 3.98 g of 2-chloroethylamine in 30 ml of diethyl ether, a solution of 3.68 g of 4-ethylphenyl isocyanate in 15 ml of tetrahydrofuran was added dropwise under ice cooling. After the resultant mixture was stirred at room temperature for 30 minutes, diethyl ether was added, followed by the collection of precipitated crystals by filtration. The crystals so obtained were added under ice cooling to a suspension of 10.8 g of 60%-sodium hydride in 35 ml of tetrahydrofuran, followed by stirring at room temperature for 15 hours. The reaction mixture was concentrated under reduced pressure, to which 1N hydrochloric acid was added. Resulting crystals were collected by filtration and washed with n-hexane, whereby 3.64 g of the title compound were obtained (yield: 89%).

Physical property data are presented in Table 1.

Referential Example 2

In a similar manner to Referential Example 1, Compounds Nos. 2 to 15 shown in Table 1 to Table 2 were synthesized using various starting materials.

TABLE 1

$$\text{R—N}\underset{\underset{}{\diagdown}}{\overset{\overset{O}{\|}}{\diagup}}\text{NH}$$

| Comp'd No. | R | Yield (%) | Melting point (°C.) | Molecular formula | Elemental analysis (%) Calculated / Found | C | H | N |
|---|---|---|---|---|---|---|---|---|
| 1 | Et—C$_6$H$_4$— | 89 | 196–198 | $C_{11}H_{14}N_2O$ | Cal. | 69.45 | 7.42 | 14.73 |
|   |   |   |   |   | Found. | 69.48 | 7.49 | 14.60 |
| 2 | CH$_3$O—C$_6$H$_4$— | 99 | 144–145 | $C_{10}H_9N_2O_2F_3$ | Cal. | 48.79 | 3.68 | 11.38 |
|   |   |   |   |   | Found. | 48.79 | 3.81 | 11.17 |
| 3 | CF$_3$—C$_6$H$_4$— | 99 | 172–173 | $C_{10}H_9N_2O_2F_3$ | Cal. | 52.18 | 3.94 | 12.17 |
|   |   |   |   |   | Found | 52.28 | 3.81 | 12.12 |
| 4 | Cl—C$_6$H$_4$— | 98 | 183–184 | $C_9H_9N_2OCl$ | Cal. | 54.97 | 4.61 | 14.25 |
|   |   |   |   |   | Found. | 54.97 | 4.67 | 14.17 |
| 5 | 3,4-F$_2$—C$_6$H$_3$— | 50 | 144–146 | $C_9H_8N_2OF_2$ | Cal. | 54.55 | 4.07 | 14.14 |
|   |   |   |   |   | Found. | 54.53 | 4.04 | 14.10 |
| 6 | 3,4-Cl$_2$—C$_6$H$_3$— | 95 | 173–174 | $C_9H_8N_2OCl_2$ | Cal. | 46.78 | 3.49 | 12.12 |
|   |   |   |   |   | Found. | 46.68 | 3.37 | 12.15 |

TABLE 1-continued

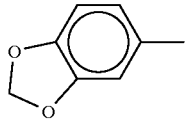

| Comp'd No. | R | Yield (%) | Melting point (° C.) | Molecular formula | Elemental analysis (%) Calculated / Found | | | |
|---|---|---|---|---|---|---|---|---|
| | | | | | | C | H | N |
| 7 | 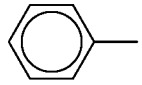 | 100 | 201–203 | C₁₀H₁₀N₂O₃ · 1/10H₂O | Cal. | 57.74 | 4.94 | 13.47 |
| | | | | | Found. | 57.44 | 4.78 | 13.29 |
| 8 | 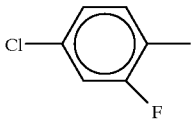 | 63 | 159–161 | C₉H₁₀N₂O | Cal. | 66.65 | 6.21 | 17.27 |
| | | | | | Found. | 66.37 | 6.16 | 17.34 |

TABLE 2

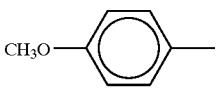

| Comp'd No. | R | Yield (%) | Melting point (° C.) | Molecular formula | Elemental analysis (%) Calculated / Found | | | |
|---|---|---|---|---|---|---|---|---|
| | | | | | | C | H | N |
| 9 |  | 82 | 122–124 | C₉H₈N₂OClF | Cal. | 50.37 | 3.76 | 13.05 |
| | | | | | Found. | 50.44 | 3.69 | 13.11 |
| 10 | 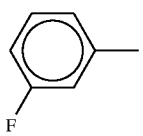 | 92 | 211–212 | C₁₀H₁₂N₂O₂ | Cal. | 62.49 | 6.29 | 14.57 |
| | | | | | Found. | 62.61 | 6.53 | 13.96 |
| 11 | 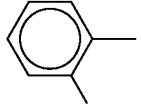 | 94 | 150–151 | C₉H₉N₂OF | Cal. | 59.99 | 5.03 | 15.55 |
| | | | | | Found | 60.24 | 5.00 | 15.58 |
| 12 | 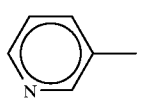 | 90 | 144–145 | C₉H₉N₂OF · 1/10H₂O | Cal. | 59.40 | 5.10 | 15.39 |
| | | | | | Found. | 59.26 | 4.93 | 15.19 |
| 13 | | 85 | 145–147 | C₁₀H₁₂N₂O₂ | Cal. | 62.49 | 6.29 | 14.57 |
| | | | | | Found. | 62.25 | 6.43 | 14.48 |
| 14 | | 75 | 156–159 | C₈H₉N₃O | Cal. | 58.89 | 5.56 | 25.75 |
| | | | | | Found. | 59.02 | 5.59 | 25.44 |

TABLE 2-continued

[Structure: R—N(ring)—NH with C=O, imidazolidinone]

| Comp'd No. | R | Yield (%) | Melting point (° C.) | Molecular formula | Elemental analysis (%) Calculated Found | | | |
|---|---|---|---|---|---|---|---|---|
| | | | | | | C | H | N |
| 15 | CH₃O—⟨phenyl⟩—⟨pyridyl-N⟩ | 65 | 152–154 | C₉H₁₁N₃O₂ | Cal. | 55.95 | 5.74 | 21.75 |
| | | | | | Found. | 55.64 | 5.73 | 21.70 |

Referential Example 3

Synthesis of α-{2-[1-(α,α,α-trifluoro-4-tolyl)-2-imidazolidinon-3-yl]ethoxy}toluene To a solution of 2-(benzyloxy)ethanol in 320 ml of dichloromethane, 35 ml of triethylamine and 19.5 ml of methanesulfonyl chloride were added under ice cooling, followed by stirring at room temperature for 2 hours. The reaction mixture was added with ice water and then extracted with dichloromethane. After the extract was washed with a saturated solution of sodium chloride, the extract was dried over magnesium sulfate and then filtered. The filtrate was concentrated under reduced pressure, whereby 49 g of 2-(benzyloxy)ethyl methanesulfonate were obtained (yield: stoichiometric).

Next, to a suspension of 6.9 g of 60%-sodium hydride in N,N-dimethylformamide, 33.0 g of 1-(α,α,α-trifluoro-4-tolyl)-2-imidazolidinone obtained in Referential Example 2 were added, followed by stirring at room temperature for 1 hour. 2-(Benzyloxy)ethyl methanesulfonate (33 g) was added and the resulting mixture was stirred at room temperature for 20 hours. The reaction mixture was added with ice water and then extracted with ethyl acetate. After the extract was washed with a saturated aqueous solution of ammonium chloride, the extract was dried over magnesium sulfate and then filtered. The filtrate was concentrated under reduced pressure. Resulting crystals were collected by filtration and then washed with n-hexane, whereby 38 g of the title compound were obtained (yield: 72%).

Melting point: 66–68° C.; NMR spectrum (CDCl₃) δ: 3.44–3.84(8H,m), 4.54(2H,s), 7.28–7.38(5H,m), 7.56(2H,d, J=8.9 Hz), 7.67(2H,d,J=8.9 Hz).

Referential Example 4

Synthesis of α-{2-[1-(4-methoxyphenyl)-2-imidazolidinon-3-yl]ethoxy}toluene

In a similar manner to Referential Example 3 except that a reaction was conducted using 1-(4-methoxyphenyl)-2-imidazolidinone in lieu of 1-(α,α,α-trifluoro-4-tolyl)-2-imidazolidinone, the title compound was obtained in a yield of 65%.

Melting point: 54–55° C.; NMR spectrum (CDCl₃) δ: 3.49–3.76(8H,m), 3.79(3H,s), 4.55(2H,s), 6.88(2H,d,J=8.9 Hz), 7.28–7.35(5H,m), 7.44(2H,d,J=8.9 Hz).

Referential Example 5

Synthesis of 2-[1-(α,α,α-trifluoro-4-tolyl)-2-imidazolidinon-3-yl]ethanol (Compound No. 16)

To a solution of 38 g of α-{2-[1-(α,α,α-trifluoro-4-tolyl)-2-imidazolidinon-3-yl]ethoxy}toluene in 400 ml of 1,4-dioxane, 15 g of 7.5% palladium carbon were added, followed by stirring under a hydrogen gas stream at 50° C. and 30 atm for 15 hours. After the reaction mixture was filtered, the filtrate was concentrated under reduced pressure. Resulting crystals were collected by filtration and then washed with ether, whereby 16.4 g of the title compound were obtained (yield: 58%).

Physical property data are presented in Table 3.

Referential Example 6

Synthesis of 2-[1-(4-methoxyphenyl)-2-imidazolidinon-3-yl]ethanol (Compound No. 17)

In a similar manner to Referential Example 5 except that a reaction was conducted using α-{2-[1-(4-methoxyphenyl)-2-imidazolidinon-3-yl]ethoxy}toluene in lieu of α-{2-[1-(α,α,α-trifluoro-4-tolyl)-2-imidazolidinon-3-yl]ethoxy}toluene, the title compound was obtained in a yield of 91%.

Physical property data are presented in Table 3.

Referential Example 7

Synthesis of 1-(4-methoxyphenyl)-4-hydroxymethyl-2-pyrrolidone (Compound No. 18)

To a solution of 9.5 g of methyl 1-(4-methoxyphenyl)-5-oxo-3-pyrrolidinecarboxylate in 80 ml of tetrahydrofuran, 1.3 g of sodium boron hydride and 12 ml of methanol were added, followed by heating under reflux for 1.5 hours. After the reaction mixture was concentrated under reduced pressure, the resultant residue was added with a 5% aqueous solution of hydrochloric acid and then extracted with dichloromethane. The extract was washed with water, dried over magnesium sulfate and then filtered. The filtrate was concentrated under reduced pressure, whereby 7.53 g of the title compound were obtained (yield: 89%).

Physical property data are presented in Table 3.

Referential Example 8

In a similar manner to Referential Example 7, Compounds Nos. 19 to 22 and 25 to 29 shown in Table 4 to Table 7 were synthesized using appropriate starting materials.

Referential Example 9

Synthesis of 1-(4-chlorophenyl)-4-hydroxymethyl-5-methyl-1H-pyrazole (Compound No. 23)

To a solution of 3.2 g of ethyl 1-(4-chlorophenyl)-5-methyl-1H-pyrazole-4-carboxylate, 0.46 g of lithium aluminum hydride was added, followed by stirring for 1.5 hours at room temperature. The reaction mixture was added with a 5% aqueous solution of hydrochloric acid and then extracted with ethyl acetate. The extract was washed with an aqueous solution of sodium chloride, dried over magnesium sulfate and then filtered. The filtrate was concentrated under reduced pressure. The residue was subjected to chromatography on a silica gel column and then purified using gradient elution with hexane-ethyl acetate, whereby 2.45 g of the title compound were obtained (yield: 91%).

Physical property data are presented in Table 5.

Referential Example 10

Synthesis of 1-(4-chlorophenyl)-3,5-dimethyl-4-hydroxymethyl-1H-pyrazole (Compound No. 24)

A reaction was conducted in a similar manner to Referential Example 9 except for the use of 1-(4-chlorophenyl)-3,5-dimethyl-1H-pyrazole-4-carboxylic acid in lieu of ethyl 1-(4-chlorophenyl)-5-methyl-1H-pyrazol-4-carboxylate, whereby the title compound was obtained in a stoichiometric yield.

Physical property data are presented in Table 5.

TABLE 3

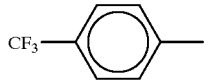

| Comp'd No. | R | A | n | m.p. (° C.) Molecular formula | Yield (%) | Elemental analysis (%) Calculated (Found) or H-NMR spectrum (CDCl$_3$)δ |
|---|---|---|---|---|---|---|
| 16 | 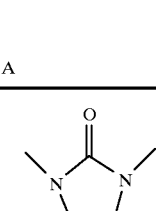 | 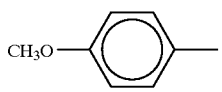 | 2 | 85–87 $C_{12}H_{13}N_2O_2F_3$ | 58 | C 52.56 (52.35  H 4.78 4.83  N 10.21 10.24) |
| 17 | 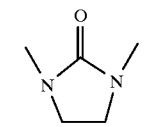 | 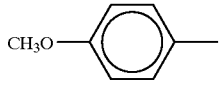 | 2 | 116–119 $C_{12}H_{16}N_2O_3$ ⅔$H_2O$ | 91 | C 59.20 (59.22  H 6.95 6.72  N 11.51 11.79) |
| 18 | 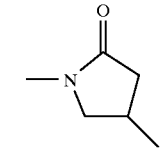 | 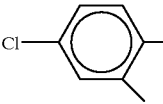 | 1 | 96–97 $C_{12}H_{15}NO_3$ | 89 | C 65.14 (64.83  H 6.83 6.91  N 6.33 6.37) |

TABLE 4

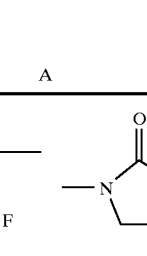

| Comp'd No. | R | A | n | m.p. (° C.) Molecular formula | Yield (%) | Elemental analysis (%) Calculated (Found) or H-NMR spectrum (CDCl$_3$)δ |
|---|---|---|---|---|---|---|
| 19 | 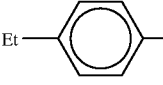 |  | 1 | Oil $C_{11}H_{11}NO_2ClF$ | 70 | 2.33–2.74(4H, m), 3.64–3.75 (3H, m), 3.89(1H, dd), 7.13–7.20(2H, m), 7.38(1H, t) |
| 20 | 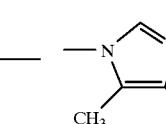 |  | 1 | 87–89 $C_{13}H_{16}N_2O$ | 87 | 1.29(3H, t), 2.17(3H, s), 2.73(2H, q), 4.65(2H, d), 7.18(2H, d), 7.32(2H, d), 7.57(1H, s) |

TABLE 4-continued

R—N(A)—(CH₂)ₙOH

| Comp'd No. | R | A | n | m.p. (° C.) Molecular formula | Yield (%) | Elemental analysis (%) Calculated (Found) or H-NMR spectrum (CDCl₃)δ | | |
|---|---|---|---|---|---|---|---|---|
| 21 | CF₃-C₆H₄- | 4,5-dimethylimidazol-1-yl | 1 | 116–117 $C_{12}H_{11}N_2OF_3$ | 92 | C 56.25 (56.19 | H 4.33 4.32 | N 10.93 10.92) |

TABLE 5

R—N(A)—(CH₂)ₙOH

| Comp'd No. | R | A | n | m.p. (° C.) Molecular formula | Yield (%) | Elemental analysis (%) Calculated (Found) or H-NMR spectrum (CDCl₃)δ | | |
|---|---|---|---|---|---|---|---|---|
| 22 | C₆H₅- | 4,5-dimethylimidazol-1-yl | 1 | 108–110 $C_{11}H_{12}N_2O$ | 48 | 2.19(3H, s), 4.65(3H, s), 7.27–7.54(5H, m), 7.57(1H, s) | | |
| 23 | Cl-C₆H₄- | 4,5-dimethylpyrazol-1-yl | 1 | 77–78 $C_{11}H_{11}N_2OCl$ | 91 | C 59.33 (59.57 | H 4.98 4.94 | N 12.58 12.56) |
| 24 | Cl-C₆H₄- | 3,4,5-trimethylpyrazol-1-yl | 1 | 109–110 $C_{12}H_{13}N_2OCl$ | Stoichiometric | 2.31(3H, s), 2.33(3H, s), 4.55(2H, s), 7.35(2H, d), 7.43(2H, d) | | |

TABLE 6

R—N(A)—(CH₂)ₙOH

| Comp'd No. | R | A | n | m.p. (° C.) Molecular formula | Yield (%) | Elemental analysis (%) Calculated (Found) or H-NMR spectrum (CDCl₃)δ | | |
|---|---|---|---|---|---|---|---|---|
| 25 | Cl-C₆H₄- | 3,5-dimethylpyrazol-1-yl | 1 | 116–117 $C_{11}H_{11}N_2OCl$ | 80 | C 59.33 (59.12 | H 4.98 5.00 | N 12.58 12.51) |

TABLE 6-continued

R—N(A)(CH$_2$)$_n$OH

| Comp'd No. | R | A | n | m.p. (° C.) Molecular formula | Yield (%) | Elemental analysis (%) Calculated (Found) or H-NMR spectrum (CDCl$_3$)δ | | |
|---|---|---|---|---|---|---|---|---|
| 26 | CF$_3$-C$_6$H$_4$- | 3,5-dimethylpyrazol-1-yl | 1 | 96–98 C$_{12}$H$_{11}$N$_2$OF$_3$ | 75 | C 56.25 (56.33 | H 4.33 4.24 | N 10.93 10.98) |
| 27 | Cl-C$_6$H$_4$- | 3,5-dimethylpyrazol-1-yl | 1 | 97–99 C$_{11}$H$_{11}$N$_2$OCl | 76 | C 59.33 (59.46 | H 4.98 4.95 | N 12.58 12.60) |

TABLE 7

R—N(A)(CH$_2$)$_n$OH

| Comp'd No. | R | A | n | m.p. (° C.) Molecular formula | Yield (%) | Elemental analysis (%) Calculated (Found) or H-NMR spectrum (CDCl$_3$)δ |
|---|---|---|---|---|---|---|
| 28 | CF$_3$-C$_6$H$_4$- | 3,5-dimethylpyrazol-1-yl | 1 | Oil C$_{12}$H$_{11}$N$_2$OF$_3$ | 79 | 2.08(1H, t), 2.37(3H, s), 4.72(2H, d), 6.24(1H, s), 7.63(4H, s) |
| 29 | C$_6$H$_5$- | 3,5-dimethylpyrazol-1-yl | 1 | Oil C$_{11}$H$_{12}$N$_2$O | 74 | 2.31(3H, s), 2.65(1H, br-s), 4.68(2H, s), 6.19(1H, s), 7.30–7.50(5H, m) |

Referential Example 11

Synthesis of 4-{2-[1-(α,α,α-trifluoro-4-tolyl)-2-imidazolidinon-3-yl]ethoxy}benzonitrile (Compound No. 30)

To a suspension of 4.4 g of 60% sodium hydride in 150 ml of anhydrous N,N-dimethylformamide, a solution of 15.0 g of 2-[1-(α,α,α-trifluoro-4-tolyl)-2-imidazolidinon-3-yl] ethanol in 300 ml of N,N-dimethylformamide obtained in Reference Example 9 was added dropwise under a nitrogen gas stream at room temperature, followed by stirring at room temperature for 1 hour. At the same temperature, a solution of 7.5 g of p-fluorobenzonitrile in 100 ml of anhydrous N,N-dimethylformamide was then added, followed by stirring for 4 hours. The reaction mixture was concentrated under reduced pressure and the resultant residue was extracted with ethyl acetate. The extract was washed with water, dried over magnesium sulfate and then filtered. The filtrate was concentrated under reduced pressure. Resulting crystals were collected by filtration and then washed with ethanol, whereby 18.6 g of the title compound were obtained (yield: 91%).

Physical property data are presented in Table 8.

Referential Example 12

In a similar manner to Referential Example 11, Compounds Nos. 31 to 35 shown in Table 8 to Table 9 were synthesized using appropriate starting materials.

TABLE 8

$$R-N\underset{(CH_2)_n}{\overset{A}{\diagup}}\!\!\!\!\!\!\!\!\!\!\!\!\!\!\!\!-\!\!\!\bigcirc\!\!\!-CN$$

| Comp'd No. | R | A | n | m.p. (° C.) Molecular formula | Yield (%) | Elemental analysis (%) Calculated (Found) or H-NMR spectrum (CDCl$_3$)δ |
|---|---|---|---|---|---|---|
| 30 | CF$_3$—⟨⟩— | imidazolidin-2-one (N,N') | 2 | 124–126 C$_{19}$H$_{16}$N$_3$O$_2$F$_3$ | 91 | C 60.80 H 4.30 N 11.19 (60.86 4.27 11.21) |
| 31 | CH$_3$—⟨⟩— | imidazolidin-2-one (N,N') | 2 | 179–181 C$_{19}$H$_{19}$N$_3$O$_3$ ¹⁄₁₀H$_2$O | 70 | C 67.28 H 5.71 N 12.39 (67.14 5.59 12.43) |
| 32 | Et—⟨⟩— | 4,5-dimethylimidazole | 1 | 105–106 C$_{20}$H$_{19}$N$_3$O | 61 | C 75.69 H 6.03 N 13.24 (75.41 6.00 13.15) |

TABLE 9

$$R-N\underset{(CH_2)_nO}{\overset{A}{\diagup}}\!\!\!\!\!\!\!\!\!\!\!\!\!\!\!\!-\!\!\!\bigcirc\!\!\!-CN$$

| Comp'd No. | R | A | n | m.p. (° C.) Molecular formula | Yield (%) | Elemental analysis (%) Calculated (Found) or H-NMR spectrum (CDCl$_3$)δ |
|---|---|---|---|---|---|---|
| 33 | CF$_3$—⟨⟩— | 4,5-dimethylimidazole | 1 | 141–142 C$_{19}$H$_{14}$N$_3$OF$_3$ ½H$_2$O | 79 | C 62.29 H 4.13 N 11.47 (62.26 3.79 11.40) |
| 34 | ⟨⟩— | 4,5-dimethylimidazole | 1 | 101–103 C$_{18}$H$_{15}$N$_3$O | 36 | C 74.72 H 5.23 N 14.52 (74.41 5.00 14.27) |
| 35 | Cl—⟨⟩— | 3,5-dimethylpyrazole | 1 | 157–159 C$_{18}$H$_{14}$N$_3$OCl | 80 | C 66.77 H 4.36 N 12.98 (66.72 4.48 12.81) |

Referential Example 13

Synthesis of 4-{2-[1-(4-ethylphenyl)-2-imidazalidinon-3-yl]ethoxy}benzaldehyde (Compound No. 36)

To a suspension of 0.50 g of 60%-sodium hydride in 20 ml of N,N-dimethylformamide, 2.0 g of 1-(4-ethylphenyl)-2-imidazolidinone obtained in Referential Example 1 were added, followed by stirring at room temperature for 1 hour. Added next were 2.9 g of 4-(2-chloroethoxy)benzaldehyde synthesized following the process disclosed in Journal of Medicinal Chemistry, 31(11), 2136, 1988. The resultant mixture was stirred at room temperature for 18 hours. The reaction mixture was added with ice water and then extracted with ethyl acetate. After the extract was washed with a saturated aqueous solution of ammonium chloride, the extract was dried over magnesium sulfate and then filtered. The filtrate was concentrated under reduced pressure. The residue was subjected to chromatography on a silica gel column and then purified using gradient elution with chloroform-ethyl acetate, whereby 580 mg of the title compound were obtained (yield: 16%).

Physical property data are presented in Table 10.

Referential Example 14

In a similar manner to Referential Example 13, Compounds Nos. 37 and 39 to 50 shown in Table 10 to Table 14 were synthesized using the compounds of Compounds Nos. 2 to 15 as starting materials.

Referential Example 15

Synthesis of 4-{3-[1-(4-chlorophenyl)-2-imidazolidinon-3-yl]propoxy}benzaldehyde (Compound No. 51)

A reaction was conducted in a manner similar to Referential Example 13 by using 1-(4-chlorophenyl)-2-imidazolidinone (Compound No. 2) in place of 1-(4-ethylphenyl)-2-imidazolidinone (Compound No. 1) and 4-(3-chloropropoxy)benzaldehyde in lieu of 4-(2-chloroethoxy)benzaldehyde, whereby the title compound was obtained in a yield of 34%.

Physical property data are presented in Table 15.

Referential Example 16

In a similar manner to Referential Example 15, Compounds Nos. 52 to 54 shown in Table 15 to Table 16 were synthesized using appropriate starting materials.

Referential Example 17

Synthesis of 4-{2-[1-(α,α,α-trifluoro-4-tolyl)-2-imidazolidinon-3-yl]ethoxy}benzaldehyde (Compound No. 38)

To a solution of 18.4 g of 4-(2-[1-(α,α,α-trifluoro-4-tolyl)-2-imidazolidinon-3-yl]ethoxy}benzonitrile obtained in Referential Example 11 in 550 ml of a 90% aqueous solution of formic acid, 18.4 g of Raney nickel were added, followed by heating under reflux for 4 hours. The reaction mixture was concentrated under reduced pressure and the resultant residue was extracted with ethyl acetate. The extract was washed with an aqueous solution of sodium bicarbonate, dried over magnesium sulfate and then filtered. The filtrate was concentrated under reduced pressure, whereby 9.9 g of the title compound were obtained (yield: 53%).

Physical property date are presented in Table 10.

Referential Example 18

In a similar manner to Referential Example 17, Compounds Nos. 45, 57 to 59 and 62 shown in Table 17 to Table 18 were synthesized using appropriate starting materials.

Referential Example 19

Synthesis of 4-{1-(4-methoxyphenyl)-2-pyrrolidon-4-yl)methoxybenzaldehyde (Compound No. 55)

To a solution of 3.0 g of 1-(4-methoxyphenyl)-4-hydroxymethyl-2-pyrrolidone obtained in Referential Example 7 in 24 ml of dichloromethane, 2.3 ml of triethylamine and 1.2 ml of methanesulfonyl chloride were added under ice cooling. The resultant mixture was stirred at room temperature for 30 minutes. The reaction mixture was concentrated under reduced pressure. The thus-obtained residue was added with water. Resulting crystals were collected by filtration and then washed with n-hexane, whereby 3.67 g of {1-(4-methoxyphenyl)-2-pyrrolidon-4-yl}methyl methanesulfonate were obtained.

Then, 3.20 g of {1-(4-methoxyphenyl)-2-pyrrolidon-4-yl}methyl methanesulfonate and 1.4 g of 4-hydroxybenzaldehyde were dissolved in 32 ml of anhydrous N,N-dimethylformamide, to which 1.92 g of anhydrous potassium carbonate were added. The resultant mixture was stirred at 70° C. for 15 hours. The reaction mixture was filtered and the filtrate was concentrated. The thus-obtained residue was extracted with ethyl acetate. The extract was washed with water, dried over magnesium sulfate and then filtered. The filtrate was concentrated under reduced pressure. The residue was subjected to chromatography on a silica gel column and then purified using gradient elution with hexane-ethyl acetate, whereby 2.86 g of the title compound were obtained (yield: 74%).

Physical property data are presented in Table 16.

Referential Example 20

In a similar manner to Referential Example 19, Compounds Nos. 56 and 63 to 66 shown in Table 16 and Table 19 to Table 20 were synthesized using appropriate starting materials.

Referential Example 21

Synthesis of 4-{1-(4-chlorophenyl)-5-methyl-1H-pyrazol-4-yl}methoxybenzaldehyde (Compound No. 60)

To a solution of 2.5 g of 1-(4-chlorophenyl)-4-hydroxymethyl-5-methyl-1H-pyrazole obtained in Referential Example 9 and 1.37 g of 4-hydroxybenzaldehyde in 60 ml of tetrahydrofuran, 3.53 g of triphenylphosphine and 2.35 g of diethyl azodicarboxylate were added under ice cooling, following by stirring at room temperature for 3 hours. The reaction mixture was concentrated under reduced pressure. The thus-obtained residue was subjected to chromatography on a silica gel column and then purified by elution with chloroform, whereby 1.43 g of the title compound were obtained (yield: 44%).

Physical property data are presented in Table 18.

Referential Example 22

Synthesis of 4-{1-(4-chlorophenyl)-3,5-dimethyl-1H-pyrazol-4-yl}methoxybenzaldehyde (Compound No. 61)

A reaction was conducted in a manner similar to Referential Example 21 except for the use of 1-(4-chlorophenyl)-

3,5-dimethyl-4-hydroxymethyl-1H-pyrazole instead of 1-(4-chlorophenyl)-4-hydroxymethyl-5-methyl1H-pyrazole, whereby the title compound was obtained in a yield of 30%.

Physical property data are presented in Table 18.

TABLE 10

R—N(A)—(CH$_2$)$_n$O—C$_6$H$_4$—CHO

| Comp'd No. | R | A | n | m.p. (° C.) Molecular formula | Yield (%) | Elemental analysis (%) Calculated (Found) or H-NMR spectrum (CDCl$_3$)δ |
|---|---|---|---|---|---|---|
| 36 | Et—C$_6$H$_4$— | imidazolidinone | 2 | 84–85<br>C$_{20}$H$_{22}$N$_2$O$_3$ | 16 | C  H  N<br>70.99  6.55  8.28<br>(70.67  6.68  8.06) |
| 37 | CF$_3$O—C$_6$H$_4$— | imidazolidinone | 2 | Oil<br>C$_{19}$H$_{17}$N$_2$O$_4$F$_3$ | 22 | 3.65–3.90(6H, m),<br>4.27(2H, d), 7.00(2H, d),<br>7.17(2H, d), 7.56(2H, d),<br>7.85(2H, d), 9.90(1H, s) |
| 38 | CF$_3$—C$_6$H$_4$— | imidazolidinone | 2 | 113–114<br>C$_{19}$H$_{17}$N$_2$O$_3$F$_3$<br>⅓H$_2$O | 53 | C  H  N<br>58.10  4.77  7.13<br>(58.25  4.64  6.74) |

TABLE 11

R—N(A)—(CH$_2$)$_n$O—C$_6$H$_4$—CHO

| Comp'd No. | R | A | n | m.p. (° C.) Molecular formula | Yield (%) | Elemental analysis (%) Calculated (Found) or H-NMR spectrum (CDCl$_3$)δ |
|---|---|---|---|---|---|---|
| 39 | Cl—C$_6$H$_4$— | imidazolidinone | 2 | 105–107<br>C$_{18}$H$_{17}$N$_2$O$_3$Cl | 21 | C  H  N<br>62.70  4.97  8.12<br>(62.54  5.00  7.84) |
| 40 | F,F—C$_6$H$_3$— | imidazolidinone | 2 | 119–120<br>C$_{18}$H$_{16}$N$_2$O$_3$F$_2$ | 38 | C  H  N<br>62.42  4.68  8.09<br>(62.41  4.62  8.07) |
| 41 | Cl,Cl—C$_6$H$_3$— | imidazolidinone | 2 | 99–102<br>C$_{18}$H$_{16}$N$_2$O$_3$Cl$_2$ | 24 | C  H  N<br>57.01  4.25  7.39<br>(56.89  4.20  7.33) |

TABLE 12

R—N(A)—(CH₂)ₙO—C₆H₄—CHO

| Comp'd No. | R | A | n | m.p. (° C.) Molecular formula | Yield (%) | Elemental analysis (%) Calculated (Found) or H-NMR spectrum (CDCl₃)δ |
|---|---|---|---|---|---|---|
| 42 | methylenedioxyphenyl | 1,3-dimethylimidazolidin-2-one | 2 | 103–105<br>$C_{19}H_{18}N_2O_5$<br>$1/10 H_2O$ | 16 | C    H    N<br>64.07  5.15  7.87<br>(63.83  4.92  7.82) |
| 43 | phenyl | 1,3-dimethylimidazolidin-2-one | 2 | 83–86<br>$C_{18}H_{18}N_2O_3$<br>$1/5 H_2O$ | 23 | C    H    N<br>68.86  5.91  8.92<br>(68.77  5.61  8.60) |
| 44 | 4-chloro-2-fluorophenyl | 1,3-dimethylimidazolidin-2-one | 2 | 86–87<br>$C_{18}H_{16}N_2O_3ClF$ | 39 | C    H    N<br>59.59  4.45  7.72<br>(59.57  4.36  7.65) |

TABLE 13

R—N(A)—(CH₂)ₙO—C₆H₄—CHO

| Comp'd No. | R | A | n | m.p. (° C.) Molecular formula | Yield (%) | Elemental analysis (%) Calculated (Found) or H-NMR spectrum (CDCl₃)δ |
|---|---|---|---|---|---|---|
| 45 | 4-methoxyphenyl-CH₂ | 1,3-dimethylimidazolidin-2-one | 2 | 113–114<br>$C_{19}H_{20}N_2O_4$ | 4 | C    H    N<br>67.05  5.92  8.23<br>(66.96  5.73  8.21) |
| 46 | 4-fluorophenyl-CH₂ | 1,3-dimethylimidazolidin-2-one | 2 | 96–98<br>$C_{18}H_{17}N_2O_3F$ | 23 | C    H    N<br>65.85  5.22  8.53<br>(65.54  5.31  8.10) |
| 47 | 3-fluorophenyl-CH₂ | 1,3-dimethylimidazolidin-2-one | 2 | 92–94<br>$C_{18}H_{17}N_2O_3F$ | 43 | C    H    N<br>65.85  5.22  8.53<br>(65.92  5.20  8.41) |

TABLE 14

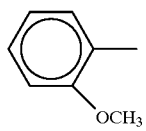

| Comp'd No. | R | A | n | m.p. (° C.) Molecular formula | Yield (%) | Elemental analysis (%) Calculated (Found) or H-NMR spectrum (CDCl₃)δ |
|---|---|---|---|---|---|---|
| 48 | 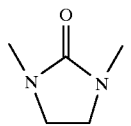 | 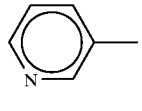 | 2 | Oil C₁₉H₂₀N₂O₄ | 8 | 3.63–3.81(6H, m), 3.83(3H, s), 4.27(2H, t), 6.89–7.35(4H, m), 7.04(2H, d), 7.85(2H, d), 9.90(1H, s) |
| 49 | 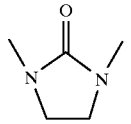 | 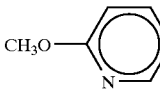 | 2 | 107–109 C₁₇H₁₇N₃O₃ | 35 | C       H       N<br>65.58   5.50    13.50<br>(65.52  5.48   13.44) |
| 50 | 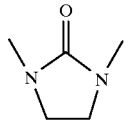 |  | 2 | 93–94 C₁₈H₁₉N₃O₄ | 21 | C       H       N<br>63.33   5.61    12.31<br>(63.27  5.63   12.27) |

TABLE 15

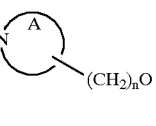

| Comp'd No. | R | A | n | m.p. (° C.) Molecular formula | Yield (%) | Elemental analysis (%) Calculated (Found) or H-NMR spectrum (CDCl₃)δ |
|---|---|---|---|---|---|---|
| 51 | 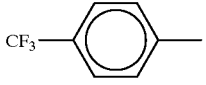 | | 3 | 91–94 C₁₉H₁₉N₂O₃Cl | 34 | C       H       N<br>63.60   5.34    7.81<br>(63.31  5.35   7.85) |
| 52 | 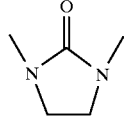 | | 3 | 80–82 C₂₀H₁₉N₂O₃F₃ | 73 | C       H       N<br>61.22   4.88    7.14<br>(61.01  4.79   7.11) |
| 53 | 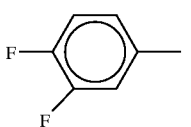 | 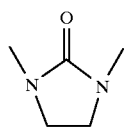 | 3 | 87–89 C₁₉H₁₈N₂O₃F₂ | 51 | C       H       N<br>63.33   5.03    7.77<br>(63.18  5.01   7.85) |

TABLE 16

R—N(A)—(CH₂)ₙO—⟨C₆H₄⟩—CHO

| Comp'd No. | R | A | n | m.p. (° C.) Molecular formula | Yield (%) | Elemental analysis (%) Calculated (Found) or H-NMR spectrum (CDCl₃)δ |
|---|---|---|---|---|---|---|
| 54 | 4-Cl, 2-Me, 6-F-phenyl | 1,3-dimethylimidazolidin-2-one | 3 | 98–100 $C_{19}H_{18}N_2O_3ClF$ | 60 | C 60.56 (60.33)  H 4.81 (4.71)  N 7.43 (7.44) |
| 55 | 4-MeO-phenyl-CH₂- | 4-methylimidazolidin-2-one | 1 | 92–94 $C_{19}H_{19}NO_4$ | 74 | C 70.14 (70.40)  H 5.89 (6.00)  N 4.30 (4.31) |
| 56 | 4-Cl, 2-Me, 6-F-phenyl | 4-methylimidazolidin-2-one | 1 | Oil $C_{18}H_{15}NO_3ClF \cdot 1/10 H_2O$ | 77 | 2.53(1H, dd), 2.83(1H, dd), 3.06(1H, m), 3.77(1H, dd), 4.04(1H, dd), 4.09–4.19(2H, m), 7.02(2H, d), 7.15–7.20(2H, m), 7.39(1H, t), 7.85(2H, d), 9.90(1H, s) |

TABLE 17

R—N(A)—(CH₂)ₙO—⟨C₆H₄⟩—CHO

| Comp'd No. | R | A | n | m.p. (° C.) Molecular formula | Yield (%) | Elemental analysis (%) Calculated (Found) or H-NMR spectrum (CDCl₃)δ |
|---|---|---|---|---|---|---|
| 57 | 4-Et-phenyl- | 4,5-dimethylimidazole (CH₃) | 1 | 76–77 $C_{20}H_{20}N_2O_2 \cdot 1/5 H_2O$ | 48 | C 74.14 (74.21)  H 6.35 (6.33)  N 8.65 (8.80) |
| 58 | 4-CF₃-phenyl- | 4,5-dimethylimidazole (Me) | 1 | 105–106 $C_{19}H_{15}N_2O_2F_3 \cdot 1/5 H_2O$ | 44 | C 62.70 (62.78)  H 4.26 (4.07)  N 7.70 (7.86) |
| 59 | phenyl- | 4,5-dimethylimidazole (CH₃) | 1 | 92–93 $C_{18}H_{16}N_2O_2 \cdot 1/5 H_2O$ | 62 | C 73.05 (73.20)  H 5.58 (5.43)  N 9.47 (9.57) |

TABLE 18

R—N⟨A⟩—(CH₂)ₙO—⟨phenyl⟩—CHO

| Comp'd No. | R | A | n | m.p. (° C.) Molecular formula | Yield (%) | Elemental analysis (%) Calculated (Found) | | or | H-NMR spectrum (CDCl₃)δ |
|---|---|---|---|---|---|---|---|---|---|
| 60 | 4-Cl-C₆H₄- | 1-pyrazolyl (5-CH₃) | 1 | 114–115 $C_{18}H_{15}N_2O_2Cl$ | 44 | C 66.16 (66.18 | H 4.63 4.52 | | N 8.57 8.55) |
| 61 | 4-Cl-C₆H₄- | 1-pyrazolyl (3,4-diCH₃) | 1 | 132–134 $C_{19}H_{17}N_2O_2Cl$ | 30 | C 66.96 (66.85 | H 5.03 4.95 | | N 8.22 8.03) |
| 62 | 4-Cl-C₆H₄- | 1-pyrazolyl (3,5-diCH₃) | 1 | Oil $C_{18}H_{15}N_2O_2Cl$ | 63 | | | | 2.35(3H, s), 5.02(2H, s), 6.39(1H, s), 7.02(2H, d), 7.39(2H, d), 7.48(2H, d), 7.86(2H, d), 9.90(1H, s) |

TABLE 19

R—N⟨A⟩—(CH₂)ₙO—⟨phenyl⟩—CHO

| Comp'd No. | R | A | n | m.p. (° C.) Molecular formula | Yield (%) | Elemental analysis (%) Calculated (Found) | | or | H-NMR spectrum (CDCl₃)δ |
|---|---|---|---|---|---|---|---|---|---|
| 63 | 4-CF₃-C₆H₄- | 1-pyrazolyl (3-CH₃) | 1 | 82–84 $C_{19}H_{15}N_2O_2F_3$ | 75 | C 63.33 (63.36 | H 4.20 4.05 | | N 7.77 7.75) |
| 64 | 4-Cl-C₆H₄- | 1-pyrazolyl (3,5-diCH₃) | 1 | 93–94 $C_{18}H_{15}N_2O_2Cl$ | 55 | C 66.16 (66.24 | H 4.63 4.64 | | N 8.57 8.69) |
| 65 | 4-CF₃-C₆H₄- | 1-pyrazolyl (3,5-diCH₃) | 1 | Oil $C_{19}H_{15}N_2O_2F_3$ | 88 | | | | 2.38(3H, s), 5.20(2H, s), 6.35(1H, s), 7.13(2H, d), 7.6–7.8(4H, m), 7.85(2H, d), 9.90(1H, s) |

TABLE 20

| Comp'd No. | R | A | n | m.p. (° C.) Molecular formula | Yield (%) | Elemental analysis (%) Calculated (Found) | or | H-NMR spectrum (CDCl$_3$)δ |
|---|---|---|---|---|---|---|---|---|
| 66 | phenyl | 3-methyl-1-methyl-pyrazol-5-yl | 1 | 81–83 C$_{18}$H$_{16}$N$_2$O$_2$ | 56 | C 73.96 (73.83) H 5.52 (5.47) | | N 9.58 9.76 |

Example 1

Synthesis of 4-{2-[1-(α,α,α-trifluoro-4-tolyl)-2-imidazolidinon-3-yl]ethoxy}benzylidene-2,4-thiazolidinedione (Compound No. 67)

A solution of 9.5 g of 4-{2-[1-(α,α,α-trifluoro4-tolyl)-2-imidazolidinon-3-yl]ethoxy}benzaldehyde obtained in Referential Example 17, 3.8 g of 2,4-thiazolidinedione and 4.3 g of sodium acetate in 50 ml of toluene was heated under reflux for 15 hours. After the reaction solvent was distilled off, 50 ml of an 80% aqueous solution of acetic acid were added. Resulting crystals were collected by filtration, whereby 9.1 g of the title compound were obtained (yield: 76%).

Physical property data are presented in Table 21.

Example 2

In a similar manner to Example 1, Compounds Nos. 68 to 87 and 93 to 97 shown in Table 21 to Table 27 and Table 29 to Table 31 were synthesized using appropriate starting materials.

Example 3

Synthesis of 5-{4-[1-(4-ethylphenyl)-5-methylimidazol-4-yl]methoxy}benzylidene-2,4-thiazolidindione (Compound No. 88)

A solution of 0.33 g of 4-[1-(4-ethylphenyl)- 5-methyl-imidazol-4-yl]methoxybenzaldehyde, 0.18 g of 2,4-thiazolidinedione and 0.05 ml of piperidine in 10 ml of ethanol was heated under reflux for 24 hours. After the reaction mixture was ice-cooled, resulting crystals were collected by filtration, whereby 0.35 g of the title compound was obtained (yield: 81%).

Physical property data are presented in Table 28.

Example 4

In a similar manner to Example 3, Compounds Nos. 89 to 92 shown in Table 28 to Table 29 were synthesized using appropriate starting materials.

Example 5

Synthesis of 4-{2-[1-(α,α,α-trifluoro-4-tolyl)-2-imidazolidinon-3-yl]ethoxy}benzyl-2,4-thiazolidindione (Compound No. 98)

To a solution of 9.0 g of 4-{2-[1-(α,α,α-trifluoro-4-tolyl)-2-imidazolidinon-3-yl]ethoxy}benzylidene-2,4-thiazolidinedione in 400 ml of 1,4-dioxane, 18 g of 7.5% palladium carbon were added, followed by stirring under a hydrogen gas stream at 50° C. and 50 atm for 12 hours. After the reaction mixture was filtered, the filtrate was concentrated under reduced pressure. Resulting crystals were collected by filtration and then washed with n-hexane, whereby 7.56 g of the title compound were obtained (yield: 80%).

Physical property data are presented in Table 32.

Example 6

In a similar manner to Example 5, Compounds Nos. 99 to 128 shown in Table 32 to Table 42 were synthesized using appropriate starting materials.

TABLE 21

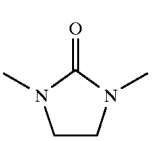

| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 67 | CF$_3$-〈ring〉- | 〈imidazolidinone〉 | 2 | 230–233 C$_{22}$H$_{18}$N$_3$O$_4$F$_3$S 4/5H$_2$O | 76 | C 53.72 (53.76 | H 4.02 4.14 | N 8.54 8.53) |
| 68 | CF$_3$O-〈ring〉- | 〈imidazolidinone〉 | 2 | 205–206 C$_{22}$H$_{18}$N$_3$O$_5$F$_3$S | 52 | C 53.55 (53.76 | H 3.68 3.78 | N 8.53 8.35) |
| 69 | Et-〈ring〉- | 〈imidazolidinone〉 | 2 | 232–235 C$_{23}$H$_{23}$N$_3$O$_4$S | 95 | C 63.14 (63.09 | H 5.30 5.08 | N 9.60 9.39) |

TABLE 22

| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 70 | Cl-〈ring〉- | 〈imidazolidinone〉 | 2 | 258–261 C$_{21}$H$_{18}$N$_3$O$_4$ClS 4/5H$_2$O | 74 | C 55.03 (55.24 | H 4.31 4.34 | N 9.17 9.15) |
| 71 | F,F-〈ring〉- | 〈imidazolidinone〉 | 2 | 231–233 C$_{21}$H$_{17}$N$_3$O$_4$F$_2$S | 92 | C 56.63 (56.71 | H 3.85 3.68 | N 9.43 9.37) |

TABLE 22-continued
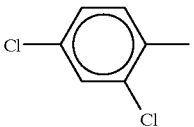
| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 72 | 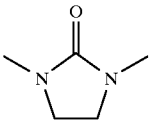 | 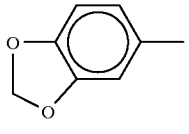 | 2 | 191–194 C$_{21}$H$_{17}$N$_3$O$_4$Cl$_2$S | 82 | C 52.73 (52.84 | H 3.58 3.50 | N 8.78 8.84) |
TABLE 23
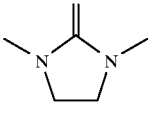
| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 73 | 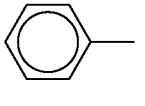 | 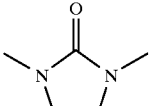 | 2 | 253–256 C$_{22}$H$_{19}$N$_3$O$_6$S | 89 | C 58.14 (58.28 | H 4.44 4.13 | N 9.25 9.15) |
| 74 | 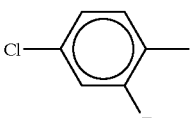 | 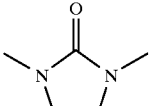 | 2 | 204–207 C$_{21}$H$_{19}$N$_3$O$_4$S | 75 | C 61.60 (61.55 | H 4.68 4.59 | N 10.26 10.04) |
| 75 | 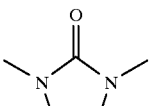 | 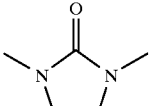 | 2 | 186–189 C$_{21}$H$_{17}$N$_3$O$_4$ClFS | 83 | C 54.61 (54.56 | H 3.71 3.57 | N 9.10 9.09) |

TABLE 24
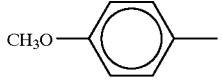
| Comp'd No. | R | A | n | m.p. (° C.) Molecular formula | Yield (%) | Elemental analysis (%) Calculated (Found) | | H-NMR spectrum (CDCl$_3$)δ or |
|---|---|---|---|---|---|---|---|---|
| 76 | 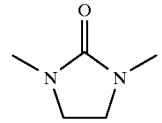 | 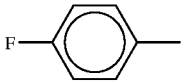 | 2 | 235–237 C$_{22}$H$_{21}$N$_3$O$_5$S | 87 | C 60.13 (60.08 | H 4.82 4.73 | N 9.56 9.44) |
| 77 | 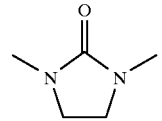 | 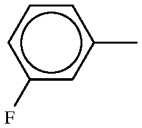 | 2 | 201–203 C$_{21}$H$_{18}$N$_3$O$_4$FS | 97 | C 59.01 (59.05 | H 4.24 4.08 | N 9.83 9.64) |
| 78 | 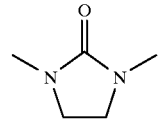 | 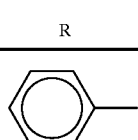 | 2 | 220–222 C$_{21}$H$_{18}$N$_3$O$_4$FS | 92 | C 59.01 (59.05 | H 4.24 4.23 | N 9.83 9.73) |
TABLE 25
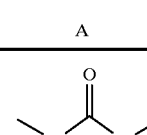
| Comp'd No. | R | A | n | m.p. (° C.) Molecular formula | Yield (%) | Elemental analysis (%) Calculated (Found) | | H-NMR spectrum (CDCl$_3$)δ or |
|---|---|---|---|---|---|---|---|---|
| 79 | 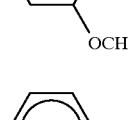 | | 2 | 199–201 C$_{22}$H$_{21}$N$_3$O$_5$S 1/10H$_2$O | 85 | C 59.88 (59.96 | H 4.84 4.86 | N 9.52 9.22) |
| 80 | 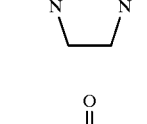 | | 2 | 269–271 C$_{20}$H$_{18}$N$_4$O$_4$S | 83 | C 58.53 (58.44 | H 4.42 4.33 | N 13.65 13.59) |

TABLE 25-continued

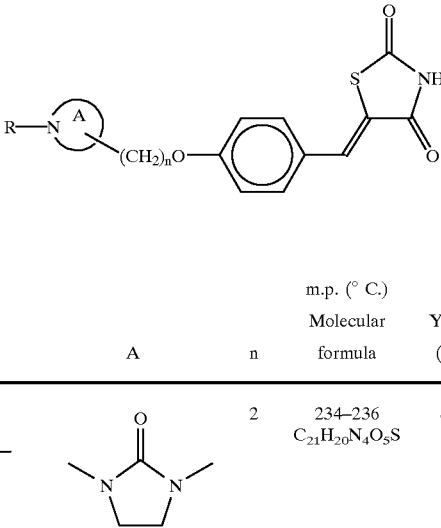

| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 81 | CH$_3$O-pyridyl | imidazolidinone | 2 | 234–236 C$_{21}$H$_{20}$N$_4$O$_5$S | 89 | C 57.26 (57.26 | H 4.58 4.46 | N 12.72 12.58) |

TABLE 26

| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 82 | Cl-phenyl | imidazolidinone | 3 | 201–202 C$_{22}$H$_{20}$N$_3$O$_4$ClS | 90 | C 57.70 (57.58 | H 4.40 4.34 | N 9.18 9.09) |
| 83 | CF$_3$-phenyl | imidazolidinone | 3 | 239–241 C$_{23}$H$_{20}$N$_3$O$_4$FS | 94 | C 56.21 (56.28 | H 4.10 4.11 | N 8.55 8.55) |
| 84 | 3,4-difluorophenyl | imidazolidinone | 3 | 204–207 C$_{22}$H$_{19}$N$_3$O$_4$F$_2$S | 78 | C 57.51 (57.70 | H 4.17 4.07 | N 9.15 8.83) |

TABLE 27

[Structure: R-N(A)-(CH2)n-O-C6H4-CH=C(thiazolidine-2,4-dione)]

| Comp'd No. | R | A | n | m.p. (° C.) Molecular formula | Yield (%) | Elemental analysis (%) Calculated (Found) | | | or H-NMR spectrum (CDCl$_3$)δ |
|---|---|---|---|---|---|---|---|---|---|
| | | | | | | C | H | N | |
| 85 | 4-Cl, 2-F-C6H3- | 1,3-dimethylimidazolidin-2-one | 3 | 193–195 $C_{22}H_{19}N_3O_4ClFS$ | 89 | 55.52 (55.67 | 4.02 3.97 | 8.83 8.70) | |
| 86 | 4-CH3O-C6H4- | N-methyl-4-methylpyrrolidin-2-one | 1 | 225–228 $C_{22}H_{20}N_2O_5S$ | 90 | 62.25 (62.26 | 4.75 4.73 | 6.60 6.59) | |
| 87 | 4-Cl, 2-F-C6H3- | N-methyl-4-methylpyrrolidin-2-one | 1 | 205–209 $C_{21}H_{16}N_2O_4ClFS$ | 93 | 56.44 (56.25 | 3.61 3.48 | 6.27 6.30) | |

TABLE 28

[Structure: R-N(A)-(CH2)n-O-C6H4-CH=C(thiazolidine-2,4-dione)]

| Comp'd No. | R | A | n | m.p. (° C.) Molecular formula | Yield (%) | Elemental analysis (%) Calculated (Found) | | | or H-NMR spectrum (CDcl$_3$)δ |
|---|---|---|---|---|---|---|---|---|---|
| | | | | | | C | H | N | |
| 88 | 4-Et-C6H4- | 4,5-dimethylimidazol-1-yl (CH3) | 1 | 187–189 $C_{23}H_{21}N_3O_3S$ 1/5H$_2$O | 81 | 65.29 (65.08 | 5.10 4.96 | 9.93 9.81) | |
| 89 | 4-CF3-C6H4- | 4,5-dimethylimidazol-1-yl (CH3) | 1 | 184–186 $C_{22}H_{16}N_3O_3F_3S$ 4/5H$_2$O | 84 | 55.76 55.70 | 3.74 3.83 | 8.87 8.43) | |

TABLE 28-continued

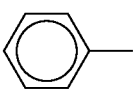

| Comp'd No. | R | A | n | m.p. (° C.) Molecular formula | Yield (%) | Elemental analysis (%) Calculated (Found) | | or | H-NMR spectrum (CDcl$_3$)δ |
|---|---|---|---|---|---|---|---|---|---|
| 90 | [phenyl] | [4,5-dimethyl-imidazol-1-yl] | 1 | 237–238 C$_{21}$H$_{17}$N$_3$O$_3$S | 61 | C 64.44 (64.33 | H 4.38 4.25 | | N 10.73 10.57) |

TABLE 29

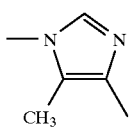

| Comp'd No. | R | A | n | m.p. (° C.) Molecular formula | Yield (%) | Elemental analysis (%) Calculated (Found) | | or | H-NMR spectrum (CDCl$_3$)δ |
|---|---|---|---|---|---|---|---|---|---|
| 91 | 4-Cl-phenyl | [4-methyl-pyrazol-1-yl] | 1 | 204–206 C$_{21}$H$_{16}$N$_3$O$_3$ClS | 61 | C 59.22 (59.35 | H 3.79 3.71 | | N 9.87 9.69) |
| 92 | 4-Cl-phenyl | [3,4,5-trimethyl-pyrazol-1-yl] | 1 | 202–204 C$_{22}$H$_{18}$N$_3$O$_3$ClS H$_2$O | 90 | C 57.70 (57.70 | H 4.40 4.23 | | N 9.18 9.00) |
| 93 | 4-Cl-phenyl | [3,5-dimethyl-pyrazol-1-yl] | 1 | 247–250 C$_{21}$H$_{16}$N$_3$O$_3$ClS 2/5H$_2$O | 53 | C 58.24 (58.45 | H 3.91 3.70 | | N 9.70 9.69) |

TABLE 30

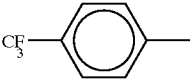

| Comp'd No. | R | A | n | m.p. (° C.) Molecular formula | Yield (%) | Elemental analysis (%) Calculated (Found) | | | H-NMR spectrum (CDCl$_3$)δ |
|---|---|---|---|---|---|---|---|---|---|
| 94 | CF$_3$—⟨phenyl⟩— | 1,5-dimethylpyrazol-3-yl | 1 | 204–207 C$_{22}$H$_{16}$N$_3$O$_3$F$_3$S | 80 | C 57.51 (57.25 | H 3.51 3.35 | N 9.15 9.24) | |
| 95 | Cl—⟨phenyl⟩— | 1,5-dimethylpyrazol-3-yl | 1 | 280–283 C$_{21}$H$_{16}$N$_3$O$_3$ClS · H$_2$O | 96 | C 56.82 (56.52 | H 4.09 3.82 | N 9.47 9.41) | |
| 96 | CF$_3$—⟨phenyl⟩— | 1,3-dimethylpyrazol-5-yl | 1 | 220–222 C$_{22}$H$_{16}$N$_3$O$_3$F$_3$S · ⅓H$_2$O | 98 | C 57.07 (56.91 | H 3.57 3.43 | N 9.07 8.87) | |

TABLE 31

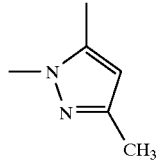

| Comp'd No. | R | A | n | m.p. (° C.) Molecular formula | Yield (%) | Elemental analysis (%) Calculated (Found) | | | H-NMR spectrum (CDCl$_3$)δ |
|---|---|---|---|---|---|---|---|---|---|
| 97 | ⟨phenyl⟩— | 1,5-dimethylpyrazol-3-yl | 1 | 260–263 C$_{21}$H$_{17}$N$_3$O$_3$S | 94 | C 64.44 (64.27 | H 4.38 4.33 | N 10.73 10.66) | |

TABLE 32

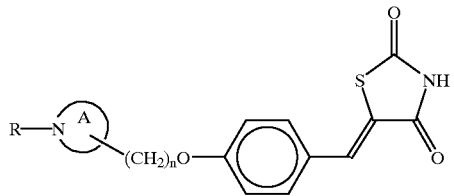

| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 98 | CF$_3$-〈phenyl〉- | imidazolidinone | 2 | 239–241 C$_{22}$H$_{20}$N$_3$O$_4$F$_3$S 4/5H$_2$O | 80 | C 53.50 (53.32 | H 4.41 4.00 | N 8.51 8.42) |
| 99 | CF$_3$O-〈phenyl〉- | imidazolidinone | 2 | 96–99 C$_{22}$H$_{20}$N$_3$O$_5$F$_3$S | 65 | C 53.33 (53.11 | H 4.07 4.14 | N 8.48 8.35) |

TABLE 33

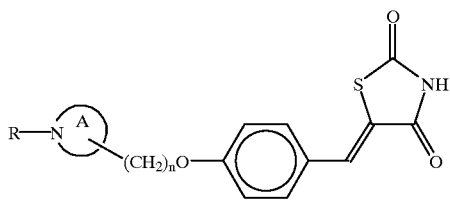

| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 100 | Et-〈phenyl〉- | imidazolidinone | 2 | 83–86 C$_{23}$H$_{25}$N$_3$O$_4$S 3/10H$_2$O | 80 | C 62.09 (62.11 | H 5.80 5.73 | N 9.44 9.32) |
| 101 | Cl-〈phenyl〉- | imidazolidinone | 2 | 247–250 C$_{21}$H$_{20}$N$_3$O$_4$ClS 4/5H$_2$O | 83 | C 54.79 (55.00 | H 4.73 4.53 | N 9.13 8.81) |
| 102 | F,F-〈phenyl〉- | imidazolidinone | 2 | 62–64 C$_{21}$H$_{19}$N$_3$O$_4$F$_2$S 3/5H$_2$O | 75 | C 55.04 (54.84 | H 4.44 4.10 | N 9.17 8.96) |

TABLE 34

[Structure: R-N(A)-(CH2)n-O-C6H4-CH=thiazolidine-2,4-dione]

| Comp'd No. | R | A | n | m.p. (° C.) Molecular formula | Yield (%) | Elemental analysis (%) Calculated (Found) | | H-NMR spectrum (CDCl$_3$)δ |
|---|---|---|---|---|---|---|---|---|
| 103 | 2,5-dichloro-4-methylphenyl | imidazolidin-2-one-1,3-diyl | 2 | 69–72 $C_{21}H_{19}N_3O_4Cl_2S$ | 74 | C 52.51 (52.57 | H 3.99 4.06 | N 8.75 8.60) |
| 104 | benzo[1,3]dioxol-5-yl-methyl | imidazolidin-2-one-1,3-diyl | 2 | 143–145 $C_{22}H_{21}N_3O_6S$ | 49 | C 58.01 (57.91 | H 4.65 4.70 | N 9.23 9.12) |
| 105 | benzyl | imidazolidin-2-one-1,3-diyl | 2 | 68–71 $C_{21}H_{21}N_3O_4S$ | 69 | C 61.30 (61.12 | H 5.14 5.16 | N 10.21 10.03) |

TABLE 35

[Structure: R-N(A)-(CH2)n-O-C6H4-CH=thiazolidine-2,4-dione]

| Comp'd No. | R | A | n | m.p. (° C.) Molecular formula | Yield (%) | Elemental analysis (%) Calculated (Found) | | H-NMR spectrum (CDCl$_3$)δ |
|---|---|---|---|---|---|---|---|---|
| 106 | 4-chloro-2-fluorophenyl-methyl | imidazolidin-2-one-1,3-diyl | 2 | 61–63 $C_{21}H_{19}N_3O_4ClFS$ | 75 | C 54.37 (54.43 | H 4.13 4.13 | N 9.06 8.94) |
| 107 | 4-methoxyphenyl-methyl | imidazolidin-2-one-1,3-diyl | 2 | 62–64 $C_{22}H_{23}N_3O_5S$ | 68 | C 59.85 (59.68 | H 5.25 5.13 | N 9.52 9.45) |

TABLE 35-continued
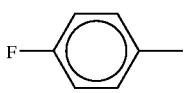
| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 108 | 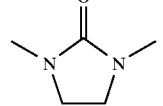 | 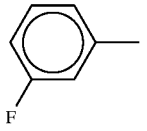 | 2 | 63–66 $C_{21}H_{20}N_3O_4FS$ | 71 | C 58.73 (58.58 | H 4.69 4.60 | N 9.78 9.66) |
TABLE 36
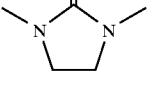
| Comp'd No. | R | A | n | m.p. (° C.) Molecular formula | Yield (%) | Elemental analysis (%) Calculated (Found) | | H-NMR spectrum or (CDCl$_3$)δ |
|---|---|---|---|---|---|---|---|---|
| 109 | 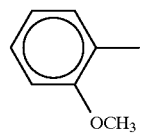 | 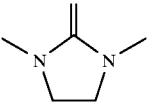 | 2 | 62–64 $C_{21}H_{20}N_3O_4FS$ | 77 | C 58.73 (58.56 | H 4.69 4.78 | N 9.78 9.59) |
| 110 | 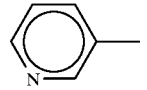 | 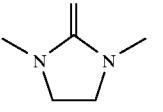 | 2 | 69–73 $C_{22}H_{23}N_3O_5S$ | 45 | C 59.37 (59.44 | H 5.30 5.09 | N 9.44 9.16) |
| 111 |  |  | 2 | 184–188 $C_{20}H_{20}N_4O_4S$ | 71 | C 58.24 (58.22 | H 4.89 4.98 | N 13.58 13.41) |

TABLE 37

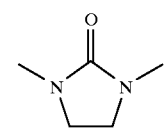

| Comp'd No. | R | A | n | m.p. (° C.) Molecular formula | Yield (%) | Elemental analysis (%) Calculated (Found) | | or | H-NMR spectrum $(CDCl_3)\delta$ |
|---|---|---|---|---|---|---|---|---|---|
| 112 | 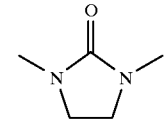 | 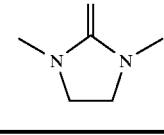 | 2 | 155–157 $C_{21}H_{22}N_4O_5S$ | 61 | C 57.00 (57.00 | H 5.01 5.03 | | N 12.66 12.56) |
| 113 | 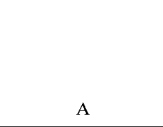 | 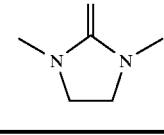 | 3 | 124–127 $C_{22}H_{22}N_3O_4ClS$ | 61 | C 57.45 (57.50 | H 4.82 4.84 | | N 9.14 9.05) |
| 114 | 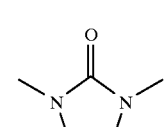 | 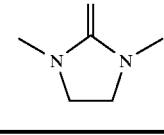 | 3 | 121–123 $C_{23}H_{22}N_3O_4F_3S$ | 74 | C 55.98 (56.19 | H 4.49 4.48 | | N 8.51 8.45) |

TABLE 38

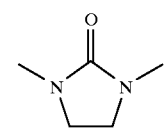

| Comp'd No. | R | A | n | m.p. (° C.) Molecular formula | Yield (%) | Elemental analysis (%) Calculated (Found) or H-NMR spectrum $(CDCl_3)\delta$ |
|---|---|---|---|---|---|---|
| 115 | (3,4-F₂-phenyl) | (1,3-dimethylimidazolidin-2-one) | 3 | 122–125 $C_{22}H_{21}N_3O_4F_2S$ | 59 | C 57.26 H 4.59 N 9.11 (57.49 4.63 9.02) |
| 116 | (3-Cl,4-F-phenyl) | (1,3-dimethylimidazolidin-2-one) | 3 | Foam $C_{22}H_{21}N_3O_4ClFS$ | 81 | 1.91–2.00(2H, m), 3.07(1H, dd), 3.20–3.80(7H, m), 3.99 (2H, t), 4.87(1H, dd), 6.88 (2H, d), 7.21(2H, d), 7.25–7.57(3H, m), 12.01(1H, brs) |

TABLE 38-continued

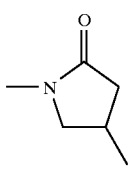

| Comp'd No. | R | A | n | m.p. (° C.) Molecular formula | Yield (%) | Elemental analysis (%) Calculated (Found) | or | H-NMR spectrum (CDCl₃)δ |
|---|---|---|---|---|---|---|---|---|
| 117 | CH₃O-C₆H₄- | N-pyrrolidinone-CH₃ | 1 | Foam C₂₂H₂₂N₂O₅S 1/5H₂O | 80 | | | 2.40(1H, dd), 2.71(1H, dd), 2.80–2.94(1H, m), 3.08 (1H, dd), 3.30(1H, dd), 3.67 (1H, dd), 3.74(3H, s), 3.95–4.40(3H, m), 4.87 (1H, dd), 6.89–6.95(4H, m), 7.16(2H, d), 7.56(2H, d), 12.01(1H, brs) |

TABLE 39

| Comp'd No. | R | A | n | m.p. (° C.) Molecular formula | Yield (%) | Elemental analysis (%) Calculated (Found) | or | H-NMR spectrum (CDCl₃)δ |
|---|---|---|---|---|---|---|---|---|
| 118 | Cl,F-C₆H₃- | N-pyrrolidinone-CH₃ | 1 | Foam C₂₁H₁₈N₂O₄ClFS | 79 | | | 2.37(1H, dd), 2.69(1H, dd), 2.93–3.06 (1H, m), 3.07–3.31(2H, m), 3.61–3.99 (2H, m), 4.04(2H, d), 4.87(1H, dd), 6.91 (2H, m), 7.17(2H, d), 7.35–7.57(3H, m), 12.00(1H, brs) |
| 119 | Et-C₆H₄- | imidazolyl-CH₃ | 1 | Foam C₂₃H₂₃N₃O₃S 2/5H₂O | 31 | | | 1.29(3H, t), 2.21(3H, s), 2.73(2H, q), 3.07(1H, dd), 3.47(1H, dd), 4.40(1H, dd), 5.02(2H, s), 7.01(2H, d), 7.16(2H, d), 7.19(2H, d), 7.32(2H, d)7.58(1H, s) |
| 120 | CF₃-C₆H₄- | imidazolyl-CH₃ | 1 | Foam C₂₂H₁₈N₃O₃F₃S 1/2H₂O | 48 | | | 2.26(3H, s), 3.10(1H, dd), 3.46(1H, dd), 4.43(1H, dd), 5.04(2H, s), 7.01(2H, d), 7.17(2H, d), 7.44(2H, d), 7.63(1H, s), 7.80(2H, d) |

TABLE 40

Structure: R-N(A)-(CH₂)ₙ-O-C₆H₄-CH₂-[thiazolidine-2,4-dione]

| Comp'd No. | R | A | n | m.p. (° C.) Molecular formula | Yield (%) | Elemental analysis (%) Calculated (Found) or | H-NMR spectrum (CDCl₃)δ |
|---|---|---|---|---|---|---|---|
| 121 | phenyl | 1-methyl-4,5-dimethyl-imidazol-2-yl | 1 | Foam $C_{21}H_{19}N_3O_3S$ | 56 | | 2.22(3H, s), 3.10(1H, dd), 3.47 (1H, dd), 4.44(1H, dd), 5.03(2H, s), 7.02(2H, d), 7.16(2H, d), 7.30(2H, d), 7.42–7.58(3H, m), 7.60(1H, s) |
| 122 | 4-Cl-phenyl | 1-methyl-4,5-dimethyl-imidazol-2-yl | 1 | 163–164 $C_{21}H_{18}N_3O_3ClS$ | 56 | | 2.35(3H, s), 3.14(1H, dd), 3.45 (1H, dd), 4.52(1H, dd), 4.93(2H, s), 6.95(2H, d), 7.18(2H, d), 7.40(2H, d), 7.46(2H, d), 7.70(1H, s), 8.20(1H, brs) |
| 123 | 4-Cl-phenyl | 1-methyl-3,4,5-trimethyl-pyrazol-2-yl | 1 | Foam $C_{22}H_{20}N_3O_3ClS$ | 24 | | 2.30(3H, s), 2.31(3H, s), 3.11(1H, dd), 3.43(1H, dd), 4.48(1H, dd), 4.86 (2H, s), 6.95(2H, d), 7.17(2H, d), 7.35–7.45(4H, m), 9.97(1H, brs) |

TABLE 41

Structure: R-N(A)-(CH₂)ₙ-O-C₆H₄-CH₂-[thiazolidine-2,4-dione]

| Comp'd No. | R | A | n | m.p. (° C.) Molecular formula | Yield (%) | Elemental analysis (%) Calculated (Found) | | | H-NMR spectrum (CDCl₃)δ |
|---|---|---|---|---|---|---|---|---|---|
| | | | | | | C | H | N | |
| 124 | 4-Cl-phenyl | 1-methyl-3,5-dimethyl-pyrazol-2-yl | 1 | 179–182 $C_{21}H_{18}N_3O_3ClS$ | 64 | 58.24 (58.45 | 3.91 3.70 | 9.70 9.69) | |
| 125 | 4-CF₃-phenyl | 1-methyl-3,5-dimethyl-pyrazol-2-yl | 1 | Foam $C_{22}H_{18}N_3O_3F_3S$ | 66 | | | | 3.07(1H, dd), 3.32(1H, dd), 4.88(1H, dd), 5.12(2H, s), 6.53(1H, s), 6.92(2H, d), 7.17(2H, d), 7.71–7.90 (4H, m), 12.01(1H, brs) |

TABLE 41-continued

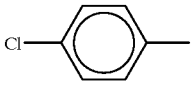

| Comp'd No. | R | A | n | m.p. (° C.) Molecular formula | Yield (%) | Elemental analysis (%) Calculated (Found) | or | H-NMR spectrum $(CDCl_3)\delta$ |
|---|---|---|---|---|---|---|---|---|
| 126 | 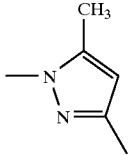 | 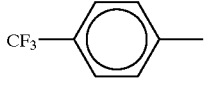 | 1 | 180–183 $C_{21}H_{18}N_3O_3ClS$ | 56 | C 58.95 (59.11 | H 4.24 3.95 | N 9.82 9.83) |

TABLE 42

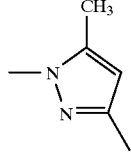

| Comp'd No. | R | A | n | m.p. (° C.) Molecular formula | Yield (%) | Elemental analysis (%) Calculated (Found) | or | H-NMR spectrum $(CDCl_3)\delta$ |
|---|---|---|---|---|---|---|---|---|
| 127 | 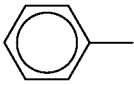 | 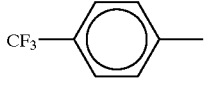 | 1 | 79–82 $C_{22}H_{18}N_3O_3F_3S$ | 57 | C 57.26 (57.20 | H 3.93 3.93 | N 9.11 9.01) |
| 128 | 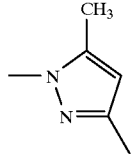 | 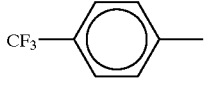 | 1 | 165–167 $C_{21}H_{19}N_3O_3S$ | 24 | C 64.11 (63.81 | H 4.87 4.63 | N 10.68 10.55) |

Test 1 (Blood-Sugar Lowering Action on Mice)

Each test compound was suspended in a 0.5% (W/V) hydroxypropyl methyl cellulose (HPMC) solution to give a concentration of 2.5 mg/me (or a concentration of 1.5 mg/ml in the case of Compound No. 102 and 0.75 mg/ml in the case of Compound No. 122). To 8–10 week old, male KK-Ay mice (purchased from Nippon Clea Inc.; 6 mice a group), the resulting suspension was forcedly administered p.o. at a rate of 0.1 ml per 10 g body weight by using an oral feeding tube. The administration of the test compound was conducted twice a day, that is, in the morning and in the evening and was continued for 5 straight days. Blood samples were collected from the candal vein of each mouse the day before the test was started and the day after the administration was finished. Each of them was placed in a blood-collecting tube in which heparin had been added beforehand. Blood sugar level of each mouse was measured by the glucose oxidase method.

From the blood sugar levels, a blood sugar-lowering rate was calculated in accordance with the below-described equation (a).

The results are presented in Table 43.

$$\text{Lowering rate (\%)} = \left[1 - \frac{\text{Blood sugar level of the medicine-administered group}}{\text{Blood sugar level of the control}}\right] \times 100 \quad \text{(a)}$$

TABLE 43

| Test compound (Comp'd No.) | Blood sugar lowering rate (%) |
|---|---|
| 98 | 41 |
| 99 | 53 |
| 101 | 34 |
| 102 | 52 |
| 122 | 21 |

Preparation Example 1: Tablets

| Compound No. 1 | 200 mg |
|---|---|
| Corn starch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated fatty acid glyceride | 4 mg |

In accordance with the above formula, tablets of 400 mg each were prepared in a manner known per se in the art.

Preparation Example 2: Granules

| Compound No. 98 | 300 mg |
|---|---|
| Lactose | 540 mg |
| Corn starch | 100 mg |
| Hydroxypropyl cellulose | 50 mg |
| Talc | 10 mg |

In accordance with the above formula, granules of 1,000 mg per wrapper were prepared in a manner known per se in the art.

Preparation Example 3: Capsules

| Compound No. 99 | 200 mg |
|---|---|
| Lactose | 30 mg |
| Corn starch | 50 mg |
| Microcrystalline cellulose | 10 mg |
| Magnesium stearate | 3 mg |

In accordance with the above formula, capsules of 293 mg each were prepared in a manner known per se in the art.

Preparation Example 4: Injection

| Compound No. 101 | 100 mg |
|---|---|
| Sodium chloride | 3.5 mg |
| Distilled water for injection | q.s. |

In accordance with the above formula, an injection of 2 ml per ampoule was prepared in a manner known per se in the art.

Preparation Example 5: Syrup

| Compound No. 102 | 200 mg |
|---|---|
| Purified sucrose | 60 mg |
| Ethyl parahydroxybenzoate | 5 mg |
| Butyl parahydroxybenzoate | 5 mg |
| Perfume | q.s. |
| Coloring matter | q.s. |
| Purified water | q.s. |

In accordance with the above formula, a syrup prepared in a manner known per se in the art.

Preparation Example 6: Suppositories

| Compound No. 122 | 300 mg |
|---|---|
| "Witepsol W-35" (registered trademark; a mixture of mono, di- and tri-glycerides of saturated fatty acids ranging from lauric acid to stearic acid; product of Dynamit Nobel Corp.) | 1400 mg |

In accordance with the above formula, suppositories were prepared in a manner known per se in the art.

I claim:

1. A thiazolidinedione derivative represented by the following formula (1):

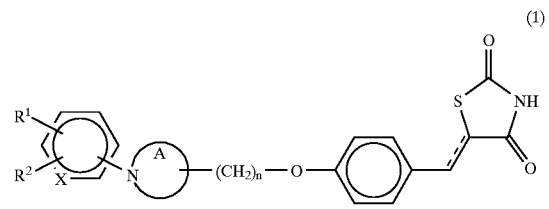

(1)

wherein $R^1$ and $R^2$ may be the same or different and individually represent a hydrogen atom, a halogen atom, a halogen-substituted or -unsubstituted lower alkyl group or a halogen-substituted or -unsubstituted lower alkoxy group, and $R^1$ and $R^2$ may be coupled together to form a ring of an alkylenedioxy chain having 1 to 3 carbon atoms; X represents a nitrogen atom or a CH group; ⋯ represents a single bond or a double bond; A represents a heterocycle selected from the following formula (a), (b), (c), (d), (e) or (f):

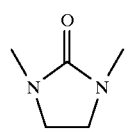

(a)

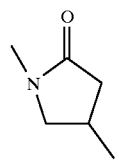

(b)

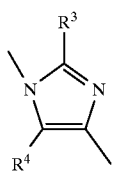
(c)

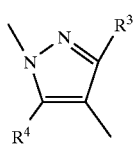
(d)

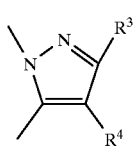
(e)

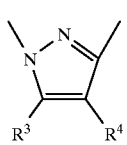
(f)

wherein R³ and R⁴ may be the same or different and individually represent a hydrogen atom or a lower alkyl group; and n stands for an integer of 1 to 4; or a salt thereof.

2. A thiazolidinedione derivative according to claim 1, wherein in the formula (1), $R^1$ and $R^2$ may be the same or different and individually represent a hydrogen atom, a halogen atom, a $C_{1-6}$ alkyl group which may be substituted by 1 to 3 halogen atoms, or a $C_{1-6}$ alkoxy group which may be substituted by 1 to 3 halogen atoms, and R1 and $R^2$ may be coupled together to form a ring of an alkylenedioxy chain having 1 to 3 carbon atoms; X represents a nitrogen atom or a CH group; ⋯ represents a single bond or a double bond; A represents a heterocycle selected from the following formula (a), (b), (c), (d), (e) or (f):

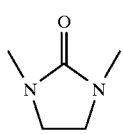
(a)

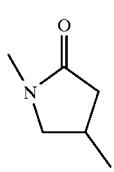
(b)

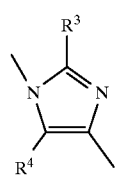
(c)

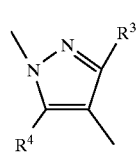
(d)

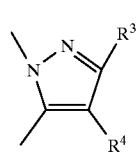
(e)

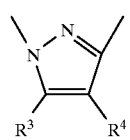
(f)

wherein $R^3$ and $R^4$ may be the same or different and individually represent a hydrogen atom or a $C_{1-6}$ alkyl group; and n stands for an integer of 1 to 4; or a salt thereof.

3. A thiazolidinedione derivative according to claim 1, wherein in the formula (1), A is a heterocycle represented by the formula (a) or (d), X is a CH group, and ⋯ is a single bond.

4. A thiazolidinedione derivative according to claim 1, wherein in the formula (1), $R^1$ and $R^2$ may be the same or different and are individually a hydrogen atom or a halogen atom, A is a heterocycle represented by the formula (d), n is 1, X is a CH group, and ⋯ is a single bond.

5. A thiazolidinedione derivative according to claim 1, wherein in the formula (1), $R^1$ is a hydrogen atom, $R^2$ is a chlorine atom, A is a heterocycle represented by the formula (d) in which $R^3$ is a hydrogen atom or a methyl group and $R^4$ is a methyl group, n is 1, X is a CH group, and ⋯ is a single bond.

6. A pharmaceutical composition comprising an effective amount of a thiazolidinedione derivative or a salt thereof as defined in claim 1 and a pharmacologically acceptable carrier.

7. A pharmaceutical composition for the treatment of diabetes, comprising an effective amount of a thiazolidinedione derivative or a salt thereof as defined in claim 1 and a pharmacologically-acceptable carrier.

8. A method for the treatment of diabetes, comprising administering to a patient an effective amount of a thiazolidinedione derivative or a salt thereof as defined in claim 1.

* * * * *